United States Patent
Suzuki

(10) Patent No.: US 9,517,016 B2
(45) Date of Patent: Dec. 13, 2016

(54) OBJECT INFORMATION ACQUIRING APPARATUS AND METHOD OF CONTROLLING THE SAME

(75) Inventor: Koichi Suzuki, Kodaira (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 121 days.

(21) Appl. No.: 14/113,422

(22) PCT Filed: Apr. 24, 2012

(86) PCT No.: PCT/JP2012/002811
§ 371 (c)(1),
(2), (4) Date: Oct. 23, 2013

(87) PCT Pub. No.: WO2012/150655
PCT Pub. Date: Nov. 8, 2012

(65) Prior Publication Data
US 2014/0051969 A1    Feb. 20, 2014

(30) Foreign Application Priority Data

May 2, 2011 (JP) .................... 2011-102842

(51) Int. Cl.
*A61B 5/05* (2006.01)
*A61B 5/00* (2006.01)
*A61B 8/00* (2006.01)
*A61B 8/08* (2006.01)

(52) U.S. Cl.
CPC ........... *A61B 5/0095* (2013.01); *A61B 5/4887* (2013.01); *A61B 8/0825* (2013.01); *A61B 8/403* (2013.01); *A61B 8/429* (2013.01); *A61B 8/5207* (2013.01)

(58) Field of Classification Search
CPC ........................ A61B 8/429; A61B 5/150954
See application file for complete search history.

(56) References Cited

U.S. PATENT DOCUMENTS

| | | | | |
|---|---|---|---|---|
| 4,887,605 A | * | 12/1989 | Angelsen et al. | 600/439 |
| 5,269,306 A | * | 12/1993 | Warnking et al. | 600/439 |
| 5,331,855 A | * | 7/1994 | Takashita et al. | 73/602 |
| 5,524,627 A | * | 6/1996 | Passi | 600/445 |

(Continued)

FOREIGN PATENT DOCUMENTS

| | | |
|---|---|---|
| JP | H02-154754 | 6/1990 |
| JP | H05-000138 | 1/1993 |

(Continued)

OTHER PUBLICATIONS

Office Action issued on May 12, 2015 in Japanese counterpart application No. 2011-702842, with translation.

*Primary Examiner* — James Kish
(74) *Attorney, Agent, or Firm* — Fitzpatrick, Cella, Harper & Scinto

(57) ABSTRACT

An object information acquiring apparatus includes a light irradiating unit that radiates light to an object to generate a photoacoustic wave, a transducer that receives the photoacoustic wave, outputs a photoacoustic signal, transmits and receives an ultrasound wave beam to and from the object, and outputs an ultrasound echo signal, a determining unit that determines whether there is an object on an optical path from the light irradiating unit, and an image processor that generates internal image data of the object using the photoacoustic signal.

21 Claims, 15 Drawing Sheets

(56) References Cited

U.S. PATENT DOCUMENTS

| | | | |
|---|---|---|---|
| 6,979,292 B2 | 12/2005 | Kanayama | 600/437 |
| 2003/0167002 A1* | 9/2003 | Nagar | A61B 5/0095 600/437 |
| 2005/0203399 A1* | 9/2005 | Vaezy et al. | 600/439 |
| 2007/0010742 A1* | 1/2007 | Torp et al. | 600/437 |
| 2007/0015978 A1 | 1/2007 | Kanayama et al. | 600/310 |
| 2008/0221647 A1 | 9/2008 | Chamberland | 607/88 |
| 2009/0234228 A1* | 9/2009 | Pintel et al. | 600/443 |
| 2010/0087733 A1 | 4/2010 | Nakajima | 600/437 |
| 2010/0094134 A1 | 4/2010 | Zhu | 600/473 |
| 2012/0190983 A1 | 7/2012 | Sandrin et al. | 600/442 |
| 2012/0209104 A1 | 8/2012 | Suzuki | 600/407 |
| 2013/0338478 A1 | 12/2013 | Hirota et al. | 600/407 |
| 2014/0018661 A1 | 1/2014 | Tsujita et al. | 600/407 |

FOREIGN PATENT DOCUMENTS

| | | |
|---|---|---|
| JP | 2003-230560 | 8/2003 |
| JP | 2008-191160 | 8/2008 |
| JP | 2009-540904 | 11/2009 |
| JP | 2012-187389 | 10/2012 |
| JP | 2012-205886 | 10/2012 |
| WO | WO 2007/148239 | 12/2007 |
| WO | WO 2011/033050 | 3/2011 |
| WO | 2011/074618 | 6/2011 |
| WO | WO 2012/014390 | 2/2012 |
| WO | WO 2012/067048 | 5/2012 |

\* cited by examiner

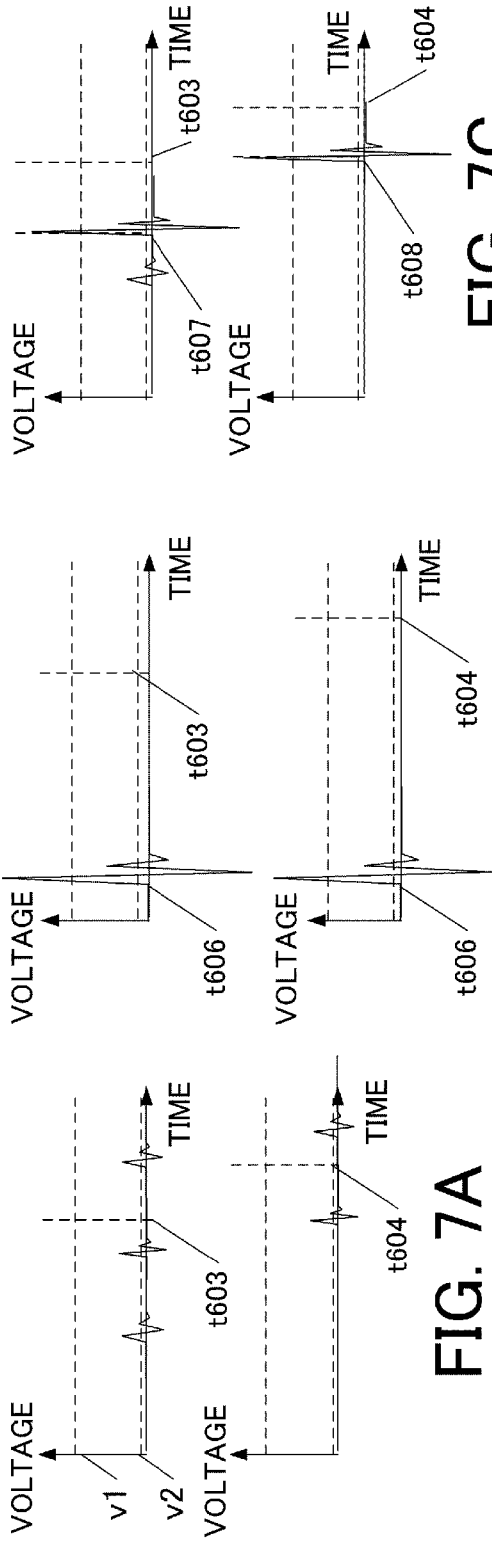
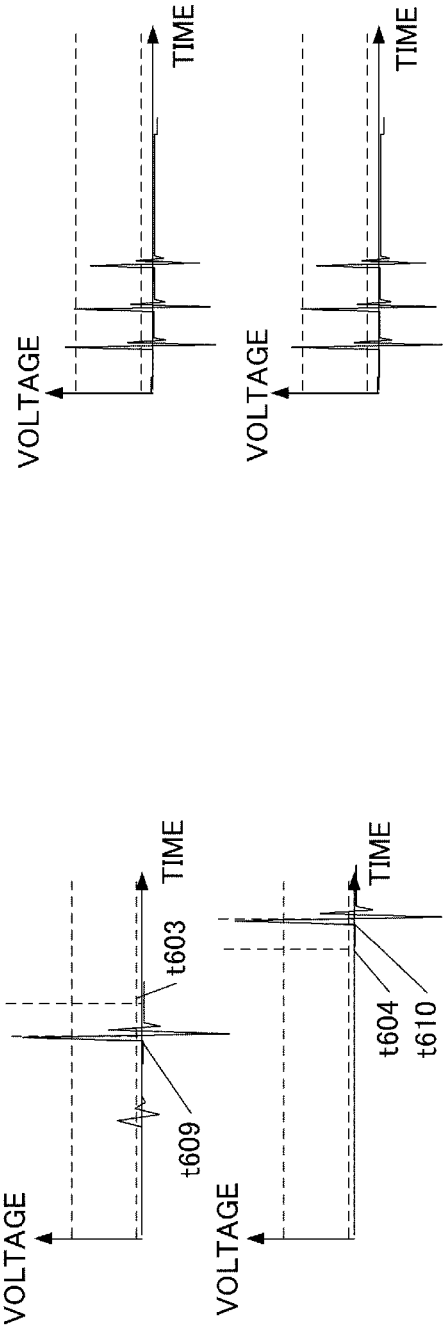
FIG. 7A
FIG. 7B
FIG. 7C
FIG. 7D
FIG. 7E

OBJECT INFORMATION ACQUIRING APPARATUS AND METHOD OF CONTROLLING THE SAME

TECHNICAL FIELD

The present invention relates to an object information acquiring apparatus and a method of controlling the same.

BACKGROUND ART

In the field of medicine, there are many studies on a photoacoustic apparatus which radiates pulsed light to an object, receives photoacoustic waves generated from the inside of the object using a probe, and changes the internal shape or function of the object into images. In addition, a photoacoustic apparatus has been proposed which can acquire photoacoustic waves and ultrasound echoes from the inside of the object and display an image in real time (PTL 1).

In the photoacoustic apparatus, the positional relation among the object, the optical path, and the probe needs to be correct in order to generate the photoacoustic waves from the inside of the object and correctly acquire the photoacoustic waves using the probe. That is, the object needs to be disposed on the optical path and come into close contact with the probe. The reason is as follows. When the object deviates from the optical path, the photoacoustic wave is not generated. When the object does not come into close contact with the probe, the photoacoustic wave is reflected between the probe and the object and does not reach the probe.

In addition, a photoacoustic apparatus has been proposed which includes a sensor for detecting the contact state between an object and a probe as one of the positional relations (PTL 2).

CITATION LIST

Patent Literature

[PTL 1]
Japanese Patent Application National Publication (Laid-Open) No. 2009-540904
[PTL 2]
Japanese Patent Application Laid-Open No. 2008-191160

SUMMARY OF INVENTION

Technical Problem

When the object deviates from the optical path, the photoacoustic wave is not generated, which makes it difficult to perform measurement. In addition, in particular, when a laser beam is used as the light source, it is necessary to pay attention to safety. For example, when the light emission hole and the transducer are provided in a handheld probe and light is emitted without contacting the probe with the object, light is likely to travel in an unintended direction. In addition, in a bed-type photoacoustic apparatus, it is not preferable that light be unnecessarily emitted when there is no object. Therefore, it is necessary to determine whether there is an object on the optical path.

As described above, in the photoacoustic apparatus according to the related art, the sensor detects the contact state between the object and the probe. However, this method can detect only the contact state of the point where the contact sensor is provided. Therefore, the method has a limitation in the accuracy of determining whether the position of the object is correct. In addition, when a large number of contact sensors are provided, the size and cost of the apparatus increase. In this method, when light is emitted from a position other than the probe, apart from when the light emission hole is included in the probe, it is difficult to determine whether there is an object on the optical path.

The invention has been made in view of the above-mentioned problems and an object of the invention is to provide an object information acquiring apparatus capable of accurately determining whether the position of an object on an optical path is correct.

Solution to Problem

The invention provides an object information acquiring apparatus comprising:
a light irradiating unit that radiates light to an object to generate a photoacoustic wave;
a probe having a transducer that receives the photoacoustic wave, outputs a photoacoustic signal, transmits and receives an ultrasound wave beam to and from the object, and outputs an ultrasound echo signal;
a determining unit that determines whether the object is disposed on an optical path from the light irradiating unit based on the ultrasound echo signal output from the transducer; and
an image processor that generates internal image data of the object using at least the photoacoustic signal.

This invention also provides a method of controlling an object information acquiring apparatus, comprising:
transmitting and receiving, by a transducer, an ultrasound wave beam to and from an object and outputting an ultrasound echo signal;
determining, by a determining unit, whether the object is disposed on an optical path from a light irradiating unit based on the ultrasound echo signal output from the transducer;
radiating, by the light irradiating unit, light to the object such that a photoacoustic wave is generated;
receiving, by the transducer, the photoacoustic wave and outputting a photoacoustic signal; and
generating, by an image processor, internal image data of the object using at least the photoacoustic signal.

Advantageous Effects of Invention

According to the invention, it is possible to provide an object information acquiring apparatus capable of accurately determining whether the position of an object on an optical path is correct.

Further features of the present invention will become apparent from the following description of exemplary embodiments with reference to the attached drawings.

BRIEF DESCRIPTION OF DRAWINGS

FIGS. 7A to 7E are diagrams illustrating examples of received signal in the first embodiment of the invention.

DESCRIPTION OF EMBODIMENTS

Figure 1:
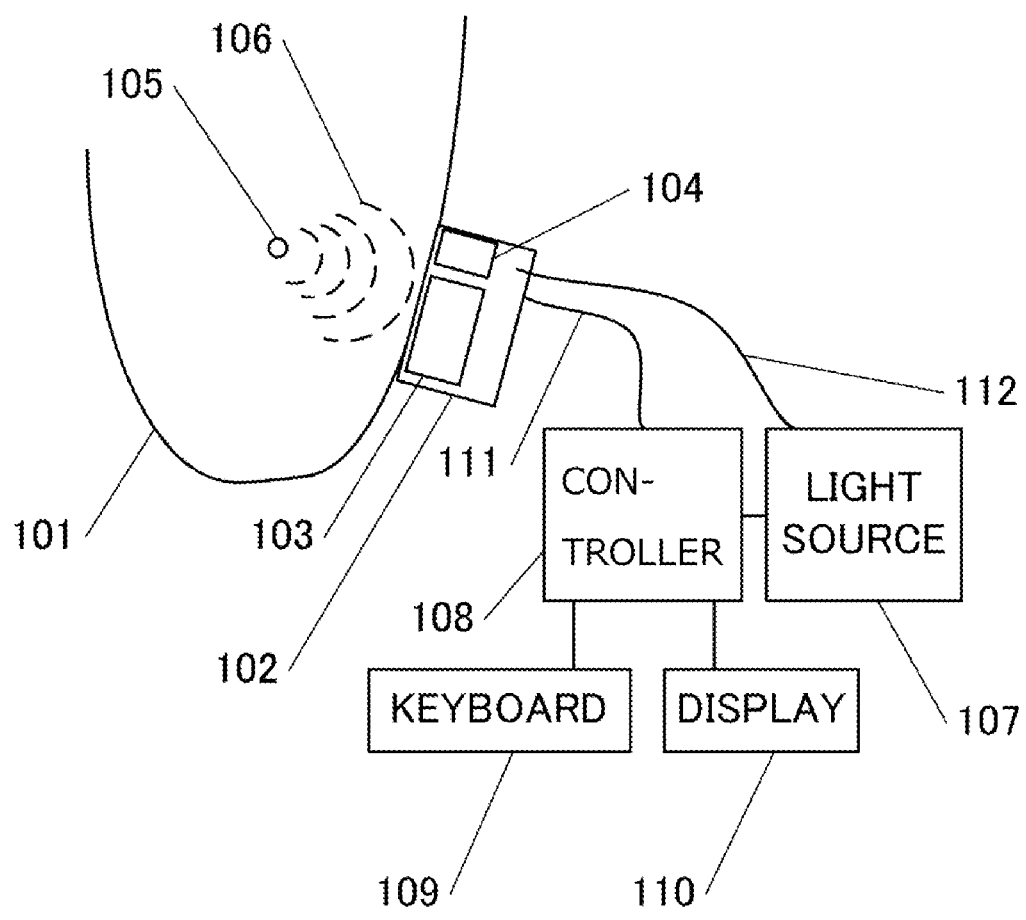
FIG. 1 is a block diagram illustrating a structure according to a first embodiment of the invention.

Hereinafter, exemplary embodiments of the invention will be described with reference to the accompanying drawings. The invention can be applied to an apparatus that uses a photoacoustic effect in which light (electromagnetic wave) is radiated to an object such that acoustic waves (which are also referred to as photoacoustic waves and are typically ultrasound waves) generated from the inside of the object are received to acquire object information as image data. This apparatus is called a photoacoustic apparatus. The photoacoustic apparatus according to the invention is configured so as to use an ultrasound echo technique which transmits ultrasound waves to an object, receives reflected waves reflected from the inside of the object, and acquires object information as image data. Therefore, the apparatus according to the invention is also called a photoacoustic apparatus and an object information acquiring apparatus which also serves as an ultrasound echo apparatus.

In the former photoacoustic apparatus, the acquired object information indicates the source distribution of the acoustic waves generated by light irradiation, an initial sound pressure distribution in the object, alight energy absorption density distribution derived from the initial sound pressure distribution, an absorption coefficient distribution, and the concentration distribution of a material forming the tissue. Examples of the concentration distribution of the material include an oxygen saturation distribution and an oxygen and reduced hemoglobin concentration distribution. When the object information acquiring apparatus is regarded as the latter ultrasound echo apparatus, the acquired object information is information to which a difference in the acoustic impedance of the tissue in the object is reflected.

The acoustic waves are typically ultrasound waves and include sound waves, ultrasound waves, acoustic waves, photoacoustic waves, and elastic waves which are called light ultra sound waves. In the invention, light indicates electromagnetic waves including visible rays and infrared rays. It is suggested that light with a specific wavelength be selected according to the component to be measured by the object information acquiring apparatus.

The object will be described below although it does not form a portion of the object information acquiring apparatus according to the invention. For example, the object information acquiring apparatus according to the invention can diagnose the malignant tumor, blood vessel disease, and blood glucose level of a human or animal or observe the progress of a chemical treatment. Therefore, a living body, specifically, the breast, finger, and feet of a human or animal can be considered as the object. A light absorber in the object indicates a part with a relatively high absorption coefficient in the object. When the human body is a measurement target, examples of the light absorber include oxygen, reduced hemoglobin, a blood vessel including them, and a malignant tumor including many new blood vessels.

First Embodiment

FIG. 1 is a block diagram illustrating a structure of a photoacoustic apparatus according to a first embodiment of the invention. In FIG. 1, reference numeral 101 is an object to be measured by the photoacoustic apparatus and is apart of the body of a subject. In this embodiment, the breast will be described as an example of the object. Reference numeral 102 is a probe and the probe 102 includes a transducer 103 which transmits and receives ultrasound waves to and from the object and a light emission hole 104 for radiating pulsed light. The transducer 103 is, for example, a PZT (Lead zirconate titanate) or a CMUT (Capacitive Micro-machined Ultrasonic Transducers) in which ultrasound sensor elements are arranged in an array. The light emission hole 104 is an emission hole of an optical fiber and may include an optical component, such as a mirror or a diffusion plate. In addition, an acoustic lens may be provided between the transducer and air.

Reference numeral 105 indicates a part (light absorber) with a high light absorption in the object and the part 105, which corresponds to, for example, a new blood vessel caused by breast cancer. When light, such as pulsed light, is radiated to the part 105, a photoacoustic wave 106 is generated by the photoacoustic effect. The photoacoustic wave 106 is converted into an electric signal by the transducer 103 which is provided in the probe 102. The electric signal is referred to as a photoacoustic signal.

Reference numeral 107 is a light source which generates the pulsed light and the light source 107 includes, for example, a YAG (Yttrium aluminum garnet) laser or a titanium-sapphire laser. A pulsed laser light source includes a flash lamp as a unit that excites a laser medium and can be electrically controlled from the outside. In addition, the pulsed laser light source has a Q-switch and can be electrically controlled from the outside. After the flash lamp is turned on at a predetermined interval from the outside to store excitation energy in the laser medium, the Q-switch is turned on, pulsed light with high energy, which is called a giant pulse, is output.

Reference numeral 108 is a controller which receives the photoacoustic signal output from the probe 102 and controls the pulse laser light source 107 and the ultrasound wave transmitting and receiving operation of the probe 105. Reference numeral 109 is a keyboard which is used by the user to instruct the photoacoustic apparatus to start measurement or to input the setting of the photoacoustic apparatus. Reference numeral 110 is a display which displays the internal image of the object to the user. Appropriate methods other than the keyboard and the display may be used as an interface with the user.

Reference numeral 111 is a cable for electrically connecting the controller 108 and the transducer 103. Reference numeral 112 is an optical fiber for guiding pulsed light from the pulsed light source 107 to the light emission hole 104. The transducer 103 radiates an ultrasound wave to the object 101 on the basis of the signal from the controller 108, receives the ultrasound wave reflected from the object 101, converts the ultrasound wave into an electric signal, and outputs the electric signal. The electric signal is referred to as an ultrasound echo signal.

In addition to the optical fiber 112, various optical members can be used to connect the light source 107 and the light emission hole 104. Examples of the optical member include a mirror which reflects light, a lens which focuses or disperses light or changes the shape of light, a prism which disperses, refracts, and reflects light, an optical fiber through which light is propagated, and a diffusion plate. Any optical member may be used as long as it can allow light emitted from the light source to be incident on the object in a desired shape.

Figure 2:
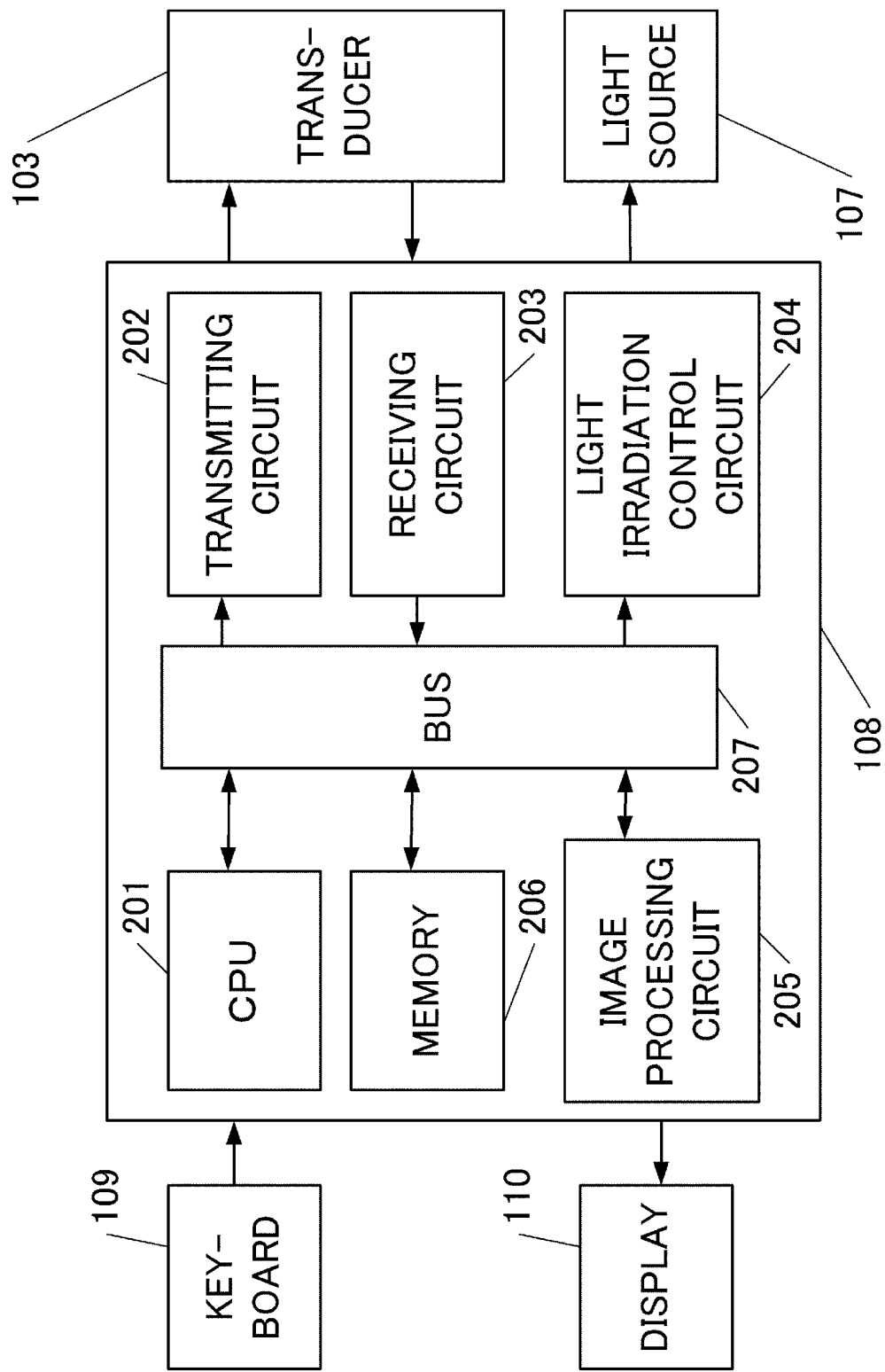
FIG. 2 is a diagram illustrating the internal structure of a controller according to the first embodiment of the invention.

FIG. 2 illustrates the internal structure of the controller 108. Reference numeral 201 is a CPU (Central processing unit) which controls the overall operation of the photoacoustic apparatus and the CPU 201 includes an embedded micro computer and software. The CPU 201 receives instructions from the user through the keyboard 109 and reflects the instructions to the operation of the apparatus. Reference numeral 202 is a transmitting circuit for transmitting a high-voltage pulse signal to the transducer and the transmitting circuit 202 includes a pulsar and a transmission memory. When an ultrasound wave is transmitted, the CPU 201 sets the amount of delay for each element of the transducer to the transmission memory. When a transmission start instruction is received, the CPU delays time by a value corresponding to the time set to the transmission memory and transmits a pulse signal to each ultrasound sensor element of the transducer 103. In this way, it is possible to control the phase of the ultrasound wave generated by each ultrasound sensor element of the transducer and electronically control the direction of the ultrasound wave. The ultrasound wave traveling in one direction is referred to as an ultrasound wave beam.

Reference numeral 203 is a receiving circuit which receives the ultrasound echo signal and the photoacoustic signal from the transducer. The receiving circuit 203 includes a pre-amplifier, an A/D converter, a reception memory, and an FPGA. The pre-amplifier amplifies the ultrasound echo signal and the photoacoustic signal. In this case, it is possible to change the gain of the pre-amplifier depending on a signal input time and acquire a weak signal generated from a deep inside the object. The amplified signal is converted into a digital value by the A/D converter and is then input to the FPGA. The FPGA performs signal processing, such as the writing of data to the reception memory, a noise removing process, and phasing and addition. When phasing and addition are performed, the phases are shifted and added for each ultrasound sensor element to generate ultrasound waves in an arbitrary direction. The ultrasound echo signal and the photoacoustic signal processed by the receiving circuit are stored in a memory 206 provided in the controller 108. Data stored in the memory 206 is referred to as ultrasound echo signal data and photoacoustic signal data.

Reference numeral 204 is a light irradiation control circuit which generates a signal for controlling the flash lamp or the Q-switch of the light source 107. When receiving a pulsed light irradiation instruction from the CPU 201, the light irradiation control circuit 204 generates a control pulse for the flash lamp and the Q-switch at a predetermined frequency and instructs the light source 107 to generate pulsed light. When receiving an instruction to stop the generation of pulsed light from the CPU 201, the light irradiation control circuit 204 stops the generation of the control pulse for the flash lamp and the Q-switch, thereby stopping the generation of the pulsed light.

Reference numeral 205 is an image processing circuit and the image processing circuit 205 generates a B-mode image from the ultrasound echo signal data. In addition, the image processing circuit 205 performs a process of reconstructing an image from the photoacoustic signal data and generates an image indicating the absorption coefficient distribution of the object 101 with respect to the pulsed light. These images are referred to as an ultrasound echo image and a photoacoustic image. The image processing circuit 205 superimposes these images and displays the superimposed image on the display 110. The image processing circuit 205 may be limited to perform up to a process of generating image data for forming an image in the previous stage of the image to be displayed to the user. Reference numeral 206 is a memory which temporarily stores signal data output from the receiving circuit 203 and data output from the image processing circuit 205. Reference numeral 207 is a bus which connects the circuits and is used for transmitting and receiving instructions to and from the CPU 201 or data to and from each circuit.

Figure 3:
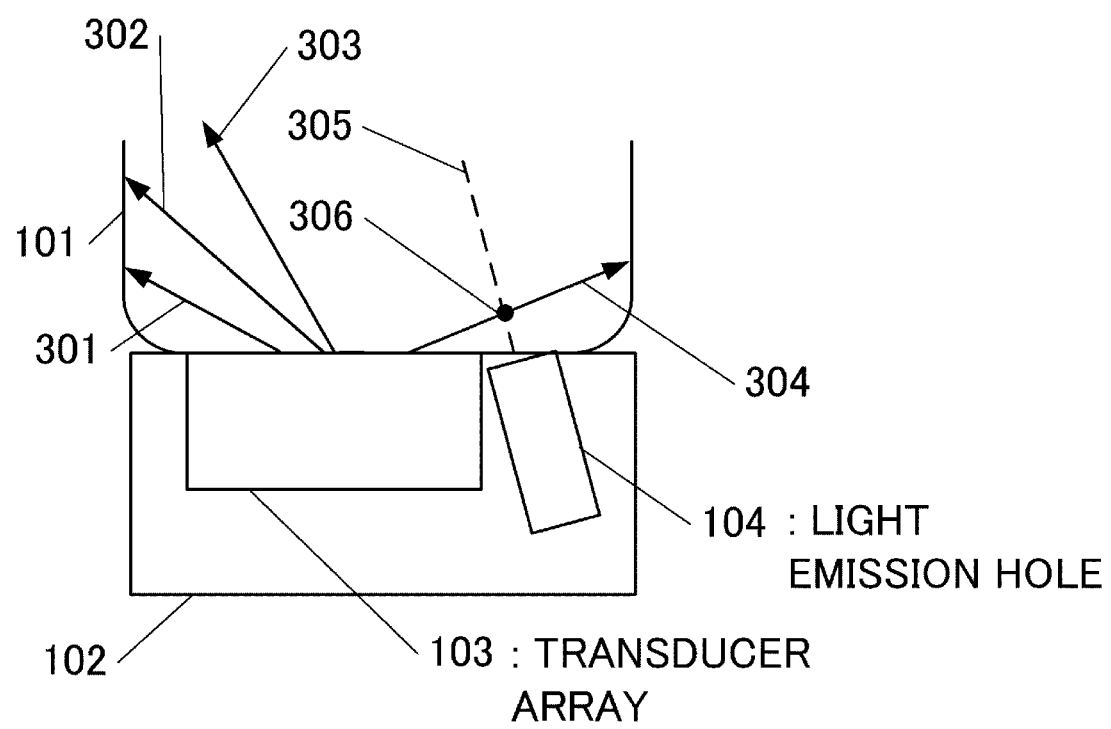
FIG. 3 is a diagram illustrating a positional relation in the vicinity of an object in the first embodiment of the invention.

FIG. 3 is a diagram illustrating a positional relation in the vicinity of the probe 102. Reference numerals 301, 302, 303, and 304 are ultrasound wave beams which are transmitted and received by the transducer. The controller 108 changes the values of the transmission memory and the reception memory in the transmitting circuit 202 and the receiving circuit 203 to perform electronic scanning with the ultrasound wave beams whenever the ultrasound wave beams are transmitted and received. For example, the controller 108 sequentially transmits and receives the ultrasound waves in the order of the ultrasound wave beams 301, 302, and 303. This operation is repeatedly performed on the entire object 101 to acquire the ultrasound echo signals in a wide range. Reference numeral 305 is an optical path of the pulsed light emitted from the light emission hole 104. The direction of the optical path is determined by the position and attachment angle of the light emission hole 104. Reference numeral 306 is an intersection point between the ultrasound wave beam 304 and the optical path 305.

Figure 4:
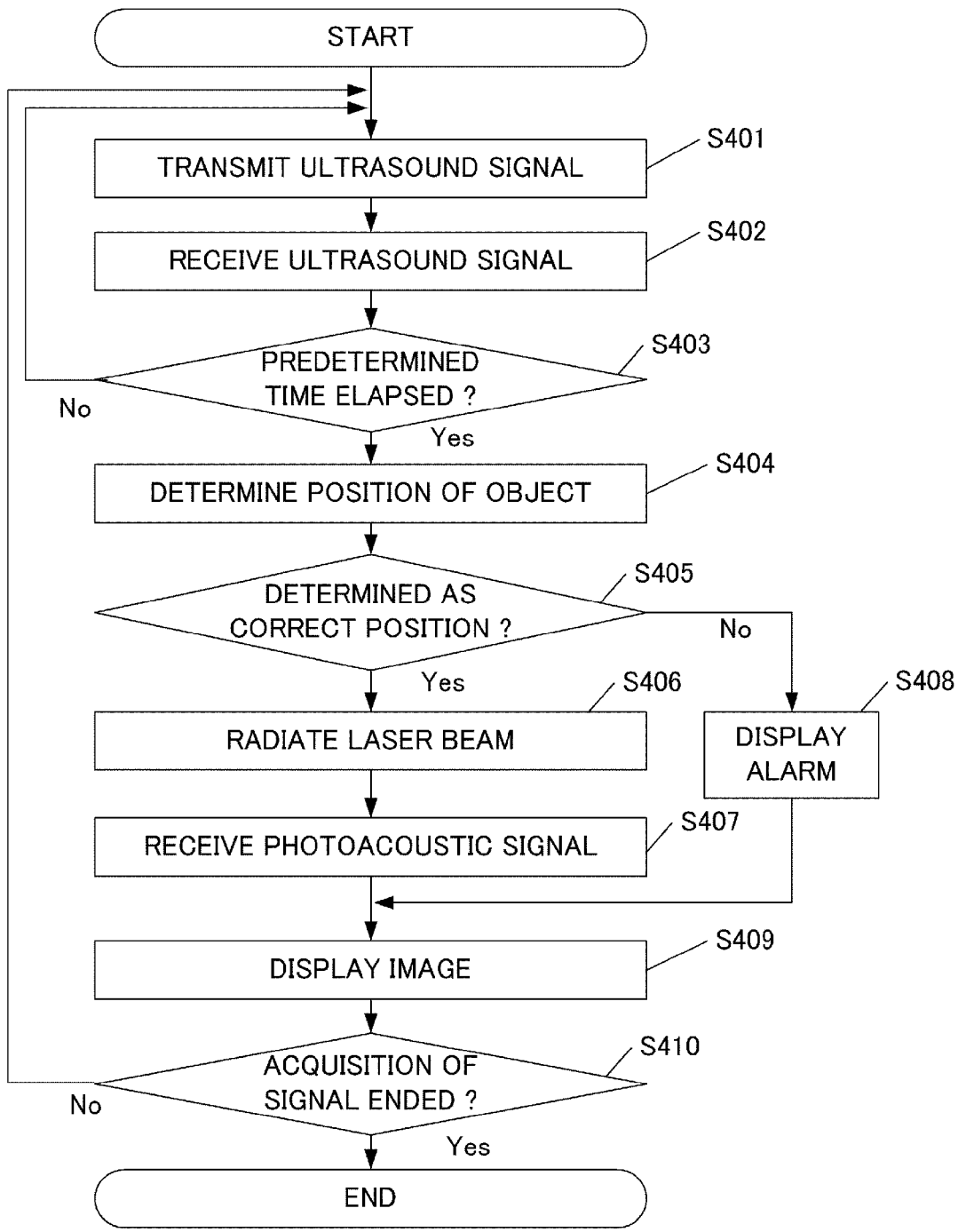
FIG. 4 is a flowchart illustrating an operation according to the first embodiment of the invention.

FIG. 4 illustrates the flow of the operation of the photoacoustic apparatus performed by the controller 108. In Step S401, the CPU 201 instructs the transmitting circuit 202 to transmit the ultrasound wave beam in the direction of 301. Then, in Step S402, the probe 102 and the receiving circuit 203 receive the ultrasound echo signal in the direction of 301, and perform processes, such as amplification, digitalization, and phasing addition. Then, the processed ultrasound echo signal is stored in the memory 206.

In Step S403, when a predetermined period of time has elapsed after the emission of pulsed light, the process proceeds to Step S404. When a predetermined period of time has not elapsed after the emission of pulsed light, the process returns to Step S401 and the ultrasound wave beams are transmitted in the next direction. In this example, after the ultrasound wave beam 301 is transmitted, the ultrasound wave beam 302 is transmitted. The predetermined period of time in Step S403 is the period for which the light source 107 radiates pulsed light. In this embodiment, it is assumed that the predetermined period of time is 100 milliseconds. In Step S403, when 100 milliseconds has elapsed after the generation of the previous pulsed light, the process proceeds to Step S404 since the light source 107 is ready to radiate the next pulsed light.

In Step S404, the CPU 201 analyzes the ultrasound echo signal data stored in the memory 206 and determines whether the object 101 is disposed at a correct position for acquiring the photoacoustic signal. That is, the CPU 201 determines whether the object 101 is on the optical path 305 and comes into contact with the probe 102. This determining process will be described in detail below. In this case, the CPU 201 operates as a determining unit. Then, in Step S405, when it is determined that the object 101 is disposed at a correct position, the process proceeds to Step S406. On the other hand, when it is determined that the object 101 is not disposed at a correct position, the process proceeds to Step S408.

In Step S406, the CPU 201 instructs the light irradiation control circuit 204 to radiate light and the light irradiation control circuit 204 directs the light source 107 to generate pulsed light. The pulsed light is emitted from the light emission hole 104 to the object 101. Then, in Step S407, the receiving circuit 203 receives the photoacoustic signal, performs processes, such as amplification, digitalization, and noise removal, and stores the processed signal in the memory 206.

When it is determined in Step S405 that the object 101 is not set at the position capable of correctly acquiring the photoacoustic signal, an alarm is displayed to the user in Step S408 and the process proceeds to Step S409. As the alarm display method, an alarm message may be displayed on the display 110, or a display unit, such as an LED which is provided separately from the display, may be turned on.

In Step S409, the image processing circuit 205 performs image processing, such as an image reconstruction process and a scan conversion process, on the basis of the ultrasound echo signal and the photoacoustic signal which are stored in the memory 206 in Steps S402 and S407. Then, the image processing circuit 205 generates an ultrasound echo image and a photoacoustic image. Then, the ultrasound echo image and the photoacoustic image are displayed on the display 110. In this case, only one of the two images may be generated and displayed on the display 110 according to the setting of the user. However, when it is determined in Step S405 that the object 101 is not set at the position capable of correctly acquiring the photoacoustic signal and the photoacoustic signal data is not stored in the memory 206, only the ultrasound echo image is displayed. Then, in Step S410, it is determined whether there is a signal acquisition end instruction from the user. When it is determined that there is a signal acquisition end instruction from the user, the process ends. When it is determined that there is no signal acquisition end instruction from the user, the process returns to Step S401 and the acquisition of the ultrasound echo signal and the photoacoustic signal is repeated.

Figure 5:
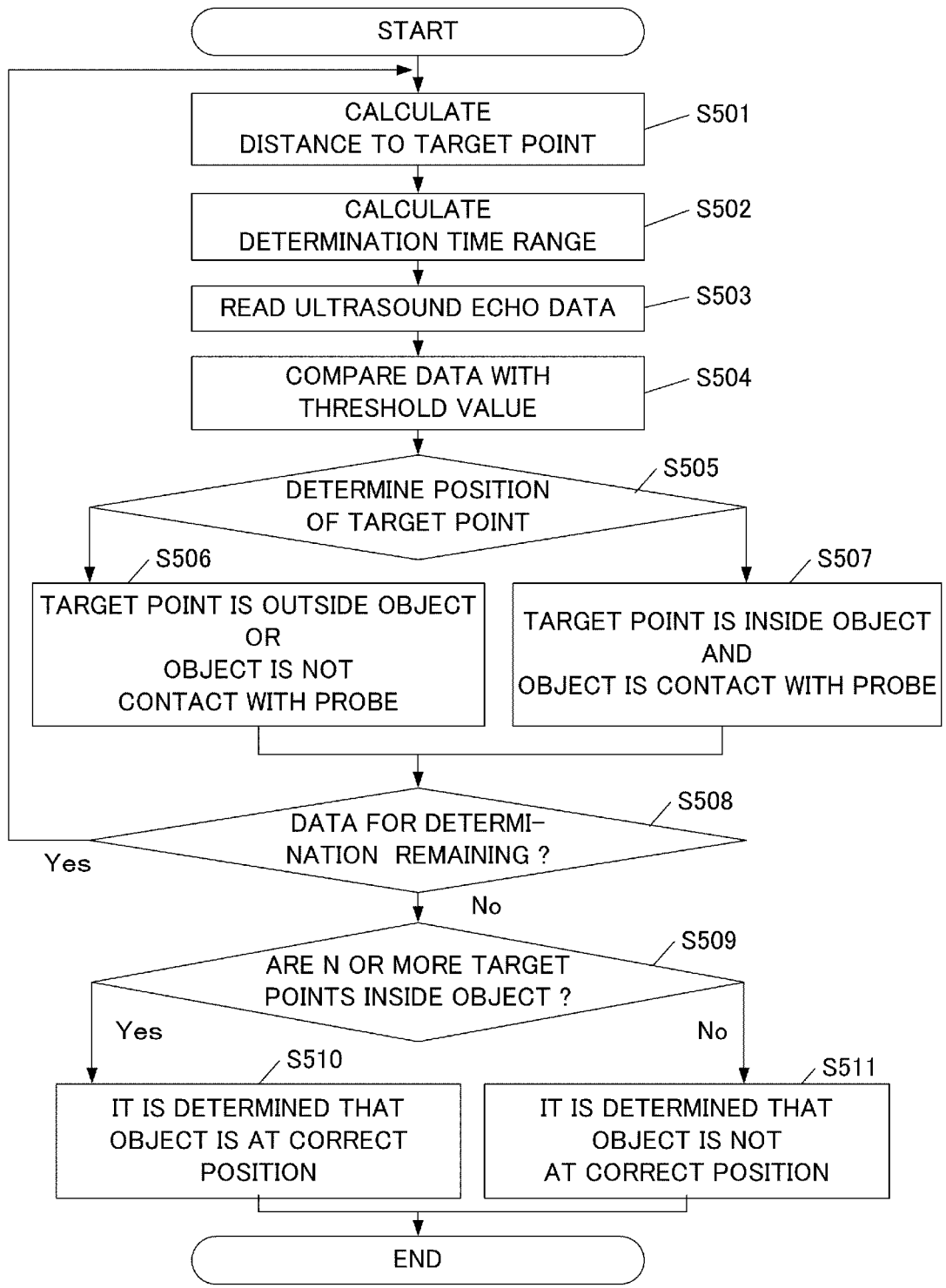
FIG. 5 is a flowchart illustrating a position determining process according to the first embodiment of the invention.

Next, the object position determining process in Step S404 will be described in detail. FIG. 5 is a flowchart illustrating the details of the determining process. FIG. 6 is a diagram illustrating examples of the positional relation between the object 101 and the probe 102.

Figure 6A:
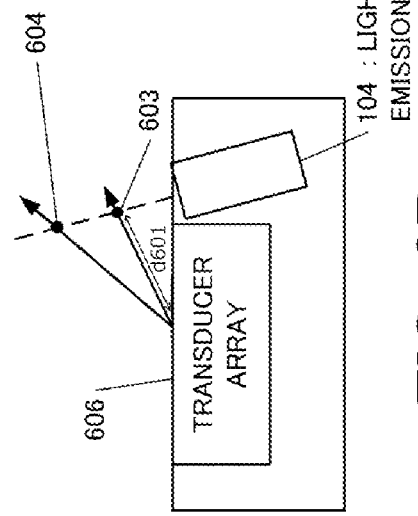
FIGS. 6A to 6D are diagrams illustrating the positional relation in the vicinity of the object in the first embodiment of the invention.
Figure 6B:
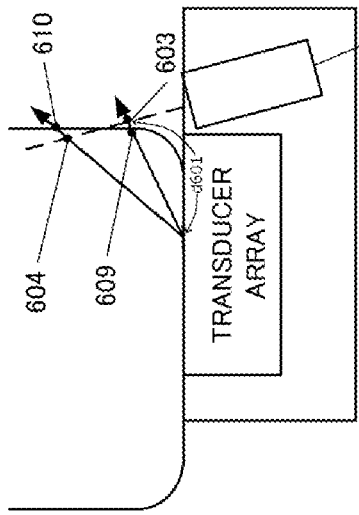
Figure 6C:
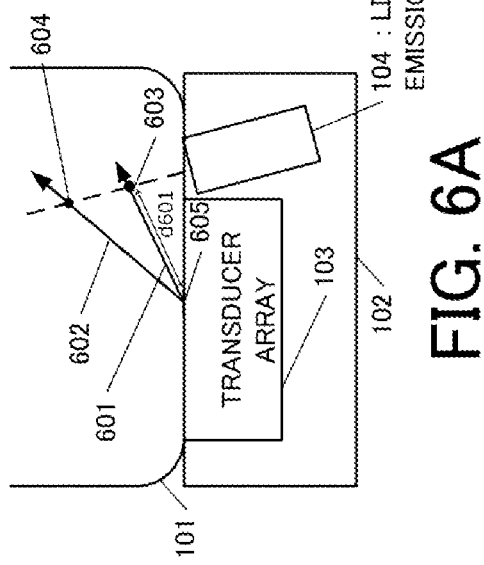
Figure 6D:
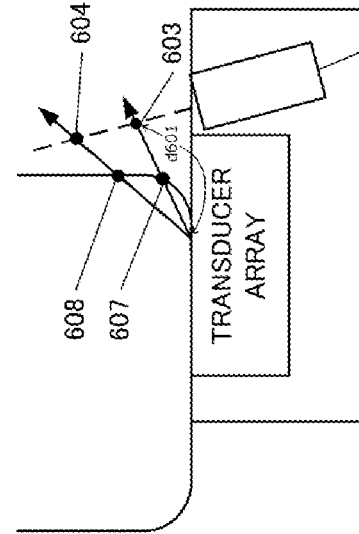

FIG. 6A illustrates an example in which the object 101 comes into contact with the entire surface of the probe 102 and light is incident on the object. FIG. 6B illustrates an example in which the object 101 is not in front of the probe. FIG. 6C illustrates an example in which the object 101 is disposed in front of the probe 102 but deviated therefrom and light is not correctly radiated. FIG. 6D illustrates a case in which the object 101 is disposed in front of the probe 102 such that a portion thereof does not come into contact with the probe 102, but light is correctly incident on the object.

In FIG. 6, reference numerals 603 and 604 are points where it is determined whether the position of the object 101 is correct and the points 603 and 604 are referred to as target points. In this embodiment, the target point is at a predetermined distance from the light emission hole on the optical path 305. It is assumed that the coordinates of the target point on the optical path are predetermined and stored in the memory 206. The determining process determines whether there are air layers between the target points 603 and 604 and the probe 102 on the basis of the ultrasound wave signal data. Reference numerals 601 and 602 are ultrasound wave beams emitted from the probe 102 to the target points 603 and 604, and the ultrasound wave beams 601 and 602 are referred to as ultrasound wave beams for determination. The target point is an intersection point between the ultrasound wave beam transmitted and received by the probe and the optical path of light emitted from the light emission hole. Reference numeral 605 is the base point of the ultrasound wave beam for determination.

FIG. 7 is a diagram illustrating ultrasound echo signals corresponding to the ultrasound wave beams 601 and 602 for determination and is a graph illustrating data which is output from the receiving circuit 203 and is then stored in the memory 206. The upper graph of FIG. 7A illustrates the ultrasound echo signal for the ultrasound wave beam 601 in the positional relation illustrated in FIG. 6A. The lower graph of FIG. 7A illustrates the ultrasound echo signal for the ultrasound wave beam 602 in the positional relation illustrated in FIG. 6A. Similarly, FIGS. 7B, 7C, and 7D correspond to FIGS. 6B, 6C, and 6D, respectively. In addition, in FIGS. 7B, 7C, and 7D, the upper graph corresponds to the ultrasound wave beam 601 and the lower graph corresponds to the ultrasound wave beam 602.

First, the flowchart illustrated in FIG. 5 will be described with reference to FIG. 6A. In Step S501, the CPU 201 reads a distance d601 from the target point 603 to the transducer from the memory 206. In FIG. 6A, the distance d601 corresponds to the distance from the target point 603 to the base point 605. It is assumed that this distance is calculated in advance on the basis of the arrangement of the light emission hole 104 and the transducer 103 in the probe 102 and the direction of the ultrasound wave beam 601 for determination and is stored in the memory 206.

Then, in Step S502, a value that is twice the distance d601 is divided by the internal sound speed of the object to calculate the time when the ultrasound echo signal is received from the target point 603. Then, the time range for determining whether there are air layers between the target points 603 and 604 and the probe 102 is calculated. This time range is referred to as a determination time range. It is assumed that the time when the ultrasound echo signal is received from the target point 603 is t603 and the time when the ultrasound echo signal is received from the target point 604 is t604 (see FIG. 7). In this embodiment, it is assumed that the determination time range of the target point 603 is from 0 to the time t603 and the determination time range of the target point 604 is from 0 to the time t604. In addition, it is assumed that the time when the transmission of the ultrasound wave beam starts is 0. Then, in Step S503, the CPU 201 reads ultrasound echo signal data corresponding to the ultrasound wave beam 601 for determination from the memory 206.

Then, in Step S504, data in the determination time range is compared with a predetermined threshold value. In Step S505, when there are M or more data items exceeding a threshold value v1 in the determination time range followed by data items that are equal to or less than a threshold value v2, the process proceeds to Step S506. Then, it is determined that the target point on the optical path is outside the object or the object does not come into contact with the probe and information indicating the determination result is stored in the memory of the CPU 201 so as to be associated with the target point. Then, the process proceeds to Step S508. M is a predetermined natural number, the threshold value v1 is greater than the ultrasound echo signal from the inside of the object, and the threshold value v2 is set to a value that is slightly greater than the noise level of the receiving circuit 203. The reason is as follows. When the surface of the object is on the ultrasound wave beam 601, most of the ultrasound waves are reflected from the surface of the object and a large amount of ultrasound echo signal data is received. As a result, a large amount of data exceeds the threshold value v1. In addition, since no ultrasound wave is transmitted to the front side of the surface of the object, the amount of ultrasound echo signal data is reduced and a large amount of data is equal to or less than the threshold value v2.

In Step S505, when the number of data items exceeding the threshold value v1 is less than M in the determination time range, or when the number of data items exceeding the threshold value v1 is equal to or more than M and the subsequent data items are more than the threshold value v2, the process proceeds to Step S507. Then, it is determined that the target point is inside the object and the object comes into contact with the probe, and information indicating the determination result is stored in the memory of the CPU 201 so as to be associated with the target point. Then, the process proceeds to Step S508.

In Step S508, it is determined whether there is other remaining ultrasound wave beam for determination. In the example illustrated in FIG. 6A, since there is the ultrasound wave beam 602 as the ultrasound wave beam for determination, the process returns to Step S501. Then, similarly to the target point 603, the positional relation between the object and the target point 604 is determined. In Step S508, when the determination operation for all the ultrasound wave beams has ended, the process proceeds to Step S509. In Step S509, when it is determined that N or more target points among the target points are inside the object and the object comes into contact with the probe, the process proceeds to Step S510 and it is determined that the object is set at a correct position. Then, the process ends. On the other hand, when it is determined that the number of target points which are in the object come into contact with the probe is less than N among the target points, the process proceeds to Step S511 and it is determined that the object is not set at a correct position. N is a predetermined natural number. Then, the process ends. In this embodiment, N is 1.

In the positional relation illustrated in FIG. 6A, there is no air between the ultrasound wave beams 601 and 602 and the target points 603 and 604 and the probe 102 comes into close contact with the object 101. Therefore, most of the transmitted ultrasound wave beams are propagated through inside the object and are gradually attenuated. In some cases, the ultra sound echo signal from the inside of the object is detected. However, as illustrated in FIG. 7A, the voltage of the received ultrasound echo signal is generally greater than the threshold value v2 and smaller than the threshold value v1. As a result, in Step S507, it is determined that the target point is inside the object and the contact between the object and the probe is sufficient. Finally, in Step S510, it is determined that the object is set at a correct position and the photoacoustic signal can be acquired.

In the positional relation illustrated in FIG. 6B, since the object 101 is absent, most of the ultrasound wave beams 601 and 602 are reflected from the boundary 606 between the surface of the probe 102 and air. A time t606 corresponds to the boundary 606. Therefore, as illustrated in FIG. 7B, a high-voltage signal appears in the vicinity of the time t606 immediately after the reception of the ultrasound echo signal starts. Thereafter, the signal level is reduced to be less than the threshold value v2. As a result, in Step S506, it is determined that the contact between the object and the probe is insufficient. Finally, in Step S511, it is determined that the object is not set at a correct position and it is difficult to acquire the photoacoustic signal.

In the positional relation illustrated in FIG. 6C, before most of the ultrasound wave beams 601 and 602 reach the target points 603 and 604, they are reflected from the boundaries 607 and 608 between the object 101 and air. If the time when the ultrasound echo signal from the boundary point 607 is received is t607 and the ultrasound echo signal from the boundary point 608 is received is t608, a high-voltage signal reflected from the boundary with air is received at the times t607 and t608. In the positional relation illustrated in FIG. 6C, since the boundary point 607 is closer to the probe than the target points 603 and the boundary point 608 is closer to the probe than the target point 604, the time t607 is shorter than the time t603 and the time t608 is shorter than the time t604. In addition, the times t607 and t608 are in the determination time range. As a result, as illustrated in FIG. 7C, a high-voltage signal appears in the determination time range and then the voltage is reduced. As a result, in Step S506, it is determined that the target points are outside the object. Finally, in Step S511, it is determined that the object is not set at a correct position and it is difficult to acquire the photoacoustic signal.

In the positional relation illustrated in FIG. 6D, before most of the ultrasound wave beams 601 for determination reach the target point 603, it is reflected from the boundary 609 between the object 101 and air. On the other hand, the ultrasound wave beam 602 for determination reaches the target point 604 and is then reflected from the boundary 610 between the object 101 and air. If the time when the ultrasound echo signal from the boundary point 609 is received is t609 and the time when the ultrasound echo signal from the boundary point 610 is received is t610, a high-voltage signal reflected from the boundary with air is received at the times t609 and t610. In the positional relation illustrated in FIG. 6D, since the boundary point 609 is closer to the probe than the target point 603, the time t609 is shorter than the time t603 and is in the determination time range. Since the boundary point 610 is away from the probe than the target point 604, the time t610 is shorter than the time t604 and is beyond the determination time range.

As a result, as illustrated in FIG. 7D, in the ultrasound echo signal corresponding to the ultrasound wave beam 601 for determination illustrated in FIG. 6D, a high-voltage signal appears in the determination time range and then the signal level is reduced. In addition, in the ultrasound echo signal corresponding to the ultrasound wave beam 602, a high-voltage signal peak does not appear in the determination time range but a strong peak appears beyond the determination time range. As a result, it is determined that the target point 603 is outside the object or the contact between the probe and the object on the ultrasound wave beam 601 for determination is insufficient. On the other hand, it is determined that the target point 604 is inside the object and the contact between the probe and the object on the ultrasound wave beam 602 for determination is sufficient. Finally, in Step S510, it is determined that the object is set at a correct position and it is possible to acquire the photoacoustic signal.

As such, the target point on the ultrasound wave beam for determination is used to determine the positional relation between the object and the probe. In this way, for example, even when it is difficult to contact the entire surface of the probe with the object, such as a peripheral part of the breast or a thin part of the arm, it is possible to determine whether the photoacoustic signal can be acquired.

In this embodiment, two ultrasound wave beams for determination are used. However, in the photoacoustic apparatus according to the invention, the number of ultrasound wave beams for determination is not limited to two. Three or more ultrasound wave beams may be used to determine the positional relation. In this case, it is possible to improve the accuracy of determination. In addition, a small number of ultrasound wave beams may be used to determine the positional relation. In this case, it is possible to reduce the time required for determination.

In this embodiment, first, the receiving circuit 203 writes ultrasound echo signal data to the memory 206 and the CPU 201 reads the ultrasound echo signal data stored in the memory and performs the object position determining process. However, the timing of the determining process according to the invention is not limited thereto. For example, in order to reduce the time required to write data to the memory, the object position determining process may be performed when the receiving circuit 203 writes data to the memory 206.

In this embodiment, when it is determined that the object is not set at the position capable of correctly acquiring the photoacoustic signal, the Q-switch of the light source is turned off to stop the radiation of pulsed light. However, a method of radiating the pulsed light according to the invention is not limited thereto. For example, a shutter may be provided outside the light source and may be closed to stop the radiation of pulsed light to the object.

In this embodiment, one light emission hole is provided next to the transducer. However, the position and number of the light emission holes in the photoacoustic apparatus in the present invention are not limited thereto. For example, the light emission holes may be provided on both sides of the transducer. Even in this way, it is possible to determine the position of the object by selecting an appropriate ultrasound wave beam for determination.

In this embodiment, the ultrasound echo signal data is compared with the threshold value in the determination time range which is determined by the positional relation between the target point and the probe, thereby determining whether the contact state between the probe and the object is correct. However, a method of determining the contact state is not limited thereto. For example, the method of comparing the threshold value may be changed depending on a depth corresponding to the vicinity of the boundary between the probe 102 and the object 101. For example, when ultrasound echo signal data greater than the threshold value v1 appears in the vicinity of the boundary between the probe 102 and the object 101, it may be determined that the positional relation between the object and the probe is as illustrated in FIG. 7B in which the object 101 does not come into contact with the probe 102. For example, when ultrasound echo signal data greater than the threshold value v1 does not appear in the vicinity of the boundary between the probe 102 and the object 101, it may be determined that the positional relation between the object and the probe is as illustrated in FIG. 7A in which the object 101 comes into contact with the probe 102.

In addition, as another determining method, for example, when ultrasound echo signal data greater than the threshold value v2 appears at a position deeper than the boundary between the probe 102 and the object 101, it may be determined that the positional relation between the object and the probe is as illustrated in FIG. 7A in which the object 101 comes into contact with the probe 102. When ultrasound echo signal data greater than the threshold value v2 does not appear at a position deeper than the boundary between the probe 102 and the object 101, it may be determined that the positional relation between the object and the probe is as illustrated in FIG. 7B in which the object 101 does not come into contact with the probe 102.

When the object 101 does not come into contact with the probe 102, the multiple reflection of ultrasound waves is likely to occur in the vicinity of the boundary between the probe and air and the periodic signals can be found. FIG. 7E is an enlarged view illustrating the vicinity of the time t606 in FIG. 7B. A frequency component of the ultrasound echo signal may be used in order to detect the multiple reflection. For example, when Fourier transform is performed on the ultrasound echo signal in the vicinity of the boundary between the probe 102 and the object 101 and a peak appears in the vicinity of a specific frequency component caused by the structure of the probe, multiple reflection occurs in the probe 102. Therefore, it may be determined that the probe 102 does not come into contact with the object 101. The specific frequency is an ultrasound wave propagation distance when an average sound speed from the transducer in the probe 102 to the acoustic lens is 2000 m/s and the thickness is 0.25 mm, and is a frequency component corresponding to 0.5 mm (2000 m/s/0.5 mm=4 MHz).

As described above, the photoacoustic apparatus according to this embodiment can determine the positional relation among the object, the probe, and the optical path using the ultrasound wave beams and determine whether the photoacoustic signal can be correctly acquired. As a result, it is possible to improve the accuracy of the acquired photoacoustic signal, which results in an improvement in diagnosis accuracy. In addition, when it is difficult to correctly acquire the photoacoustic signal, no pulsed light is radiated. Therefore, it is possible to improve the life span and safety of the apparatus. This effect is similarly obtained from either case in which the light emission hole and the transducer are provided in a handheld probe or a bed-type photoacoustic apparatus.

Second Embodiment

Next, a second embodiment of the invention will be described. The second embodiment differs from the first embodiment in that two compression plates 813 and 815 are provided between the object and the probe. The two compression plates are used to hold the object therebetween.

Figure 8:
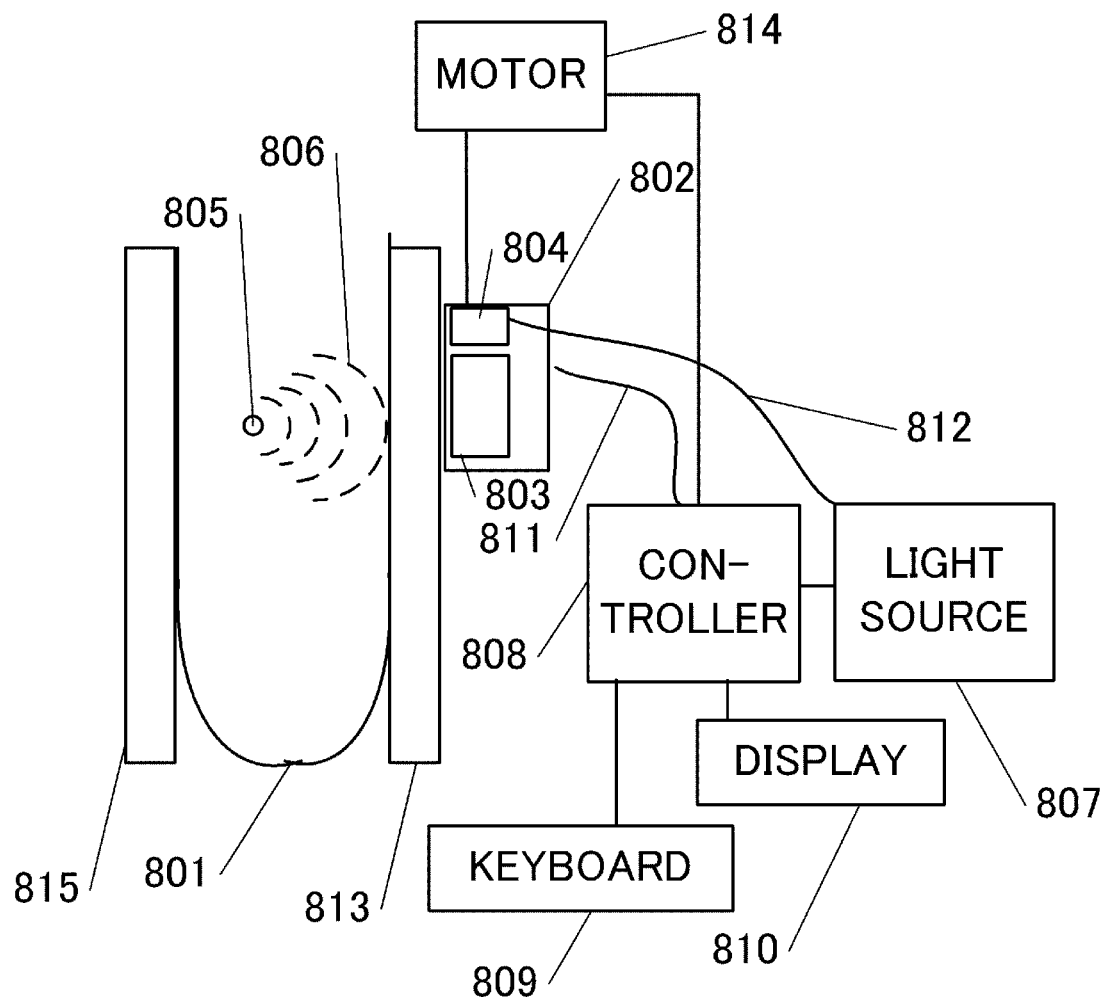
FIG. 8 is a block diagram illustrating a structure according to a second embodiment of the invention.

FIG. 8 is a block diagram illustrating the structure of a photoacoustic apparatus according to the second embodiment of the invention. In FIG. 8, an object 801, a probe 802, a transducer 803, a light emission hole 804, a light absorption part 805, a photoacoustic wave 806, a light source 807, a keyboard 809, a display 810, a cable 811, and an optical fiber 812 are the same as those in the first embodiment and thus the description thereof will not be repeated. Reference numerals 813 and 815 are compression plates for fixing the object therebetween. The compression plates to be used are made of a material with high transmittance with respect to light and ultrasound waves. Reference numeral 814 is a mechanism (scanning unit) for two-dimensionally scanning the probe 802 and the mechanism 814 includes, for example, a motor, a two-dimensional stage, and an encoder.

In the photoacoustic apparatus according to the second embodiment of the invention, the user fixes the object 801 between the compression plates in advance and operates the keyboard 809 to input a measurement start instruction. The controller 808 receives the measurement start instruction and moves the probe 802 to scan the surface of the object 801 using the motor 814 while contacting the probe 802 with the compression plate 813. The probe acquires an ultrasound echo signal and a photoacoustic signal according to the flow illustrated in FIG. 4 while being moved.

Figure 14:
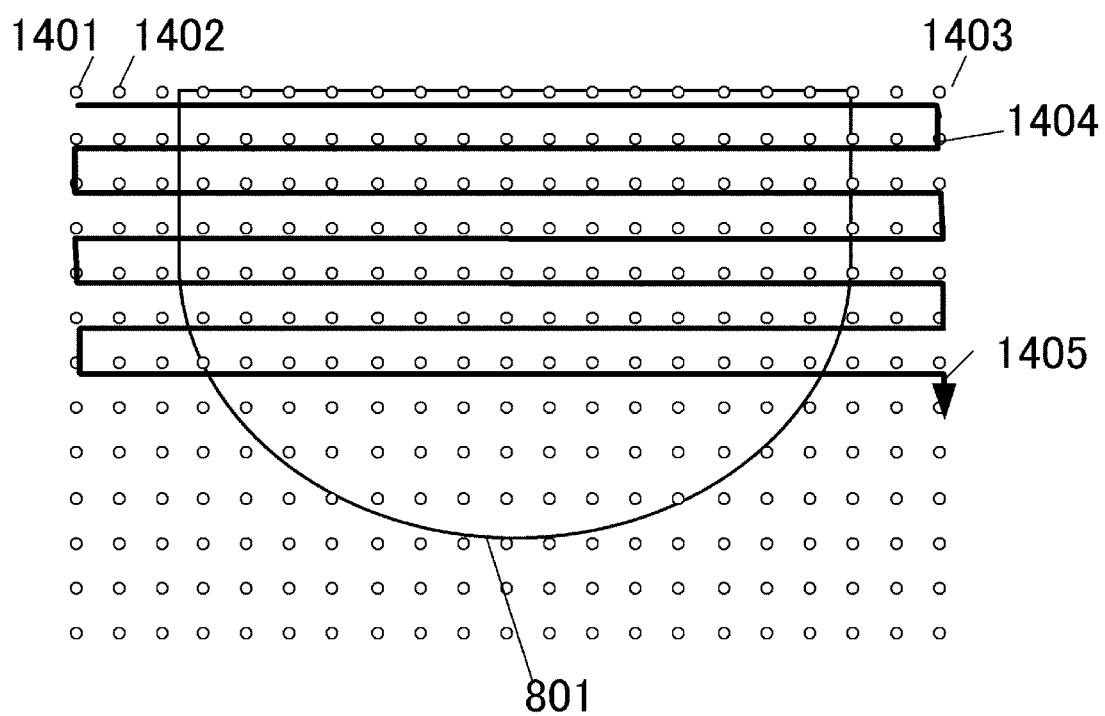
FIG. 14 is a diagram illustrating measurement points and a moving direction in the second embodiment of the invention.

The position on the object 801 where the photoacoustic signal is acquired and the moving direction of the probe 802 will be described with reference to FIG. 14. Hereinafter, the position where the photoacoustic signal is acquired is referred to as a measurement point. FIG. 14 is a diagram illustrating the object 801, as viewed from the probe 802. Points 1401, 1402, 1403, and 1404 and the other points in FIG. 14 are the measurement points. The measurement points are present on the entire surface of the object 801. An arrow 1405 indicates the moving direction of the probe 802. The photoacoustic apparatus according to this embodiment acquires the photoacoustic signal at the measurement point 1401 first and moves the probe 802 to the measurement point 1402 in the horizontal direction. This operation is repeatedly performed to acquire the photoacoustic signal at the measurement point 1403. Then, the probe 802 is moved to the measurement point 1404 in the vertical direction. Then, this operation is repeatedly performed to acquire the photoacoustic signals in the entire region of the object 801.

Figure 9:
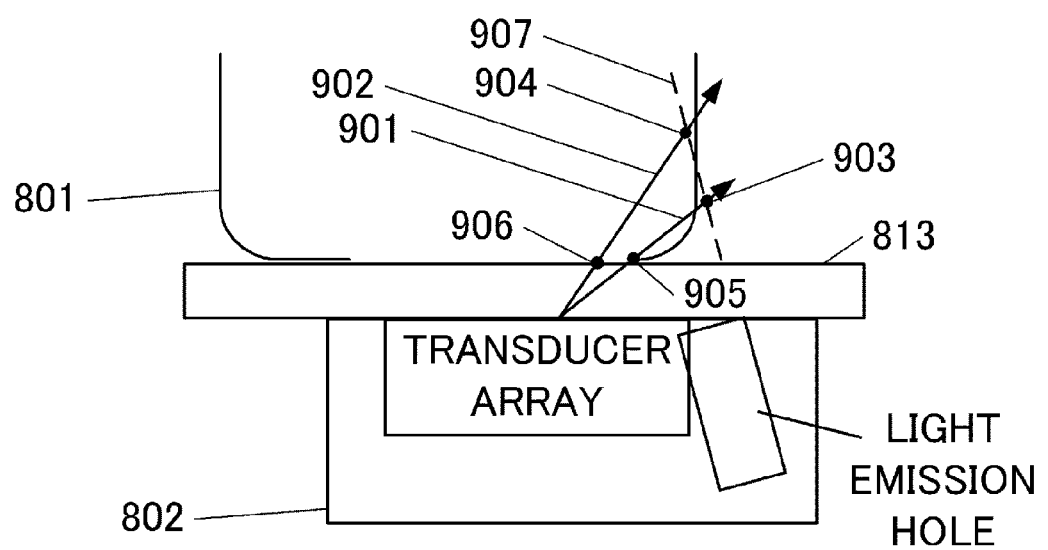
FIG. 9 is a diagram illustrating a positional relation in the vicinity of an object in the second embodiment of the invention.

FIG. 9 is an enlarged view illustrating the periphery of the object 801 and the probe 802 in the second embodiment of the invention. Reference numerals 901 and 902 are ultrasound wave beams for determination. Reference numeral 903 is a target point on the ultrasound wave beam 901 for determination. In this embodiment, the target point 903 is an intersection point between the ultrasound wave beam 901 for determination and an optical path 907. Reference numeral 904 is a target point on the ultrasound wave beam 902 for determination. In this embodiment, the target point 904 is an intersection point between the ultrasound wave beam 902 and the optical path 907. Reference numeral 905 is an intersection point between the ultrasound wave beam 901 and an object-side surface of the compression plate 813. Reference numeral 906 is an intersection point between the ultrasound wave beam 902 and the object-side surface of the compression plate 813. The points 905 and 906 are referred to as determination start points.

Figure 10:
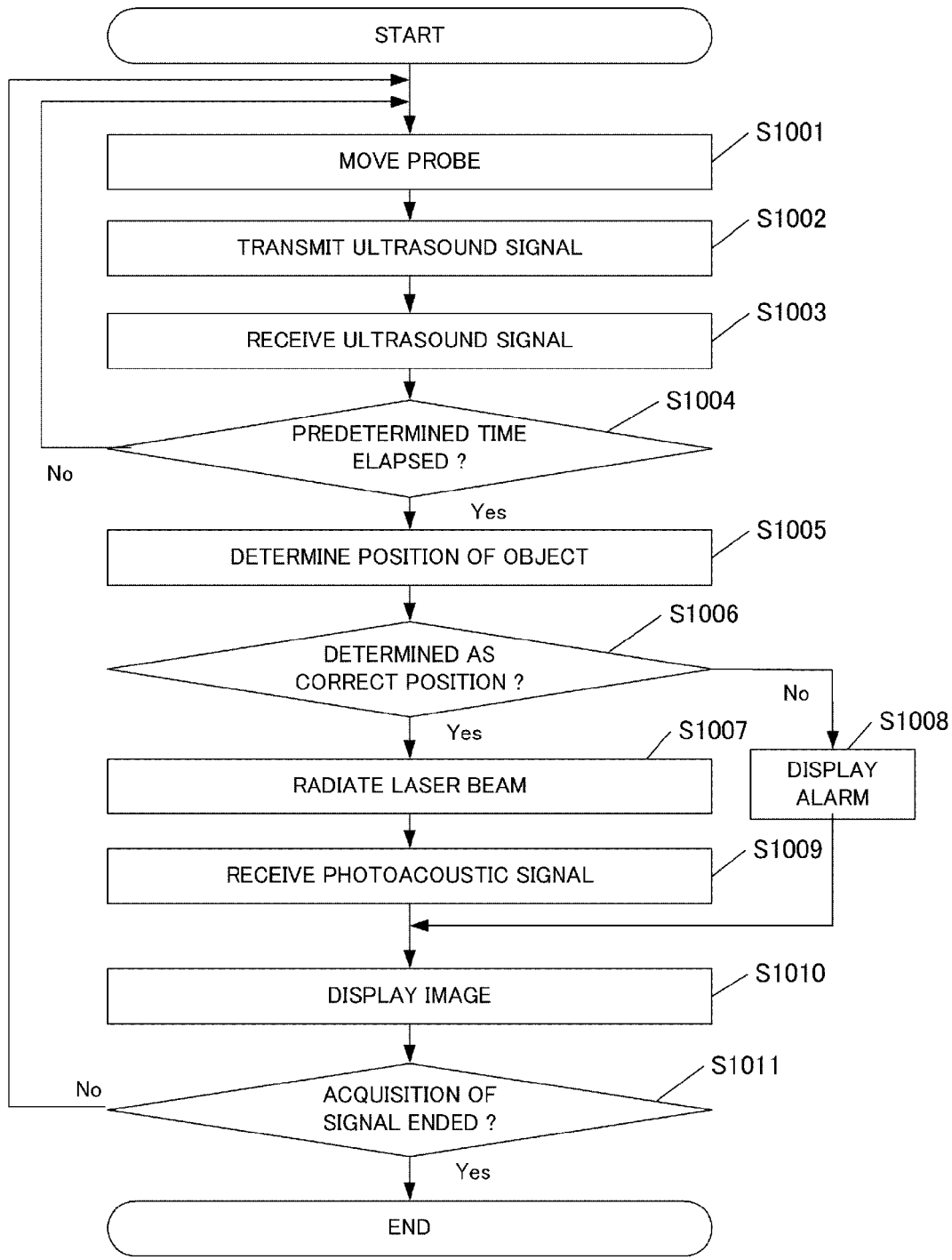
FIG. 10 is a flowchart illustrating an operation according to the second embodiment of the invention.

FIG. 10 illustrates the flow of an operation according to the invention. In Step S1001, the CPU 201 outputs an instruction to the motor 814 to move the probe to a position where the photoacoustic signal of the object 801 is acquired. Then, in Steps S1002 to S1004, similarly to Steps S401 to S403, ultrasound echo signal data is acquired. In Step S1004, when a certain period of time has elapsed from the generation of the previous pulsed light, the process proceeds to Step S1005 since the light source 807 is ready to radiate the next pulsed light. On the other hand, in Step S1004, when a certain period of time has not elapsed from the generation of the previous pulsed light, the process returns to Step S1001 and the probe 802 is moved to the next measurement point.

In Step S1005, the CPU 201 analyzes the ultrasound echo signal data stored in the memory 206 and determines whether the object 801 is set at a correct position. This process according to this embodiment differs from that according to the first embodiment in that the determination time range is corrected for the thickness of the compression plate 813. Then, in Steps S1006 to S1010, similarly to Steps S405 to S409 in the first embodiment, photoacoustic signal data is acquired. Finally, in Step S1011, it is determined whether the acquisition of the ultrasound echo signal data and the photoacoustic signal data at all of the measurement points of the object 801 is completed. When it is determined that the acquisition is completed, a message indicating the end of the measurement is notified to the user and the process ends. When it is determined that the acquisition is not completed, the process returns to Step S1001 and the probe 802 is moved to the next measurement point.

The flow of the determining process in Step S1005 according to this embodiment is the same as the flow of the operation according to the first embodiment illustrated in FIG. 5. However, a method of calculating the determination time range in Step S502 is different from that in the first embodiment. In the first embodiment, in Step S502, the period from the time when the reception of the ultrasound echo signal starts to the time when the ultrasound echo returns from the target point to the probe is the determination time range. However, in this embodiment, the period from the time when the transmitted ultrasound wave passes through the determination start point 905 or 906 to the time when the ultrasound echo from the target point 903 or 904 returns to the probe 802 is the determination time range. That is, the ultrasound echo signal generated from the compression plate 813 is ignored. In this way, it is possible to prevent the influence of the reflected echo of the ultrasound wave beams 901 and 902 between the compression plate 813 and the probe 802 and thus accurately determine whether the object 801 blocks the optical path.

<Modification>

In this embodiment, the probe scans all of the predetermined measurement points, as illustrated in FIG. 14, regardless of the result of the object position determining process. However, the scanning range may be limited according to the result of the object position determining process. For example, the probe may not be in front of the object and the movement of the probe to the measurement point which is not suitable to acquire the photoacoustic signal may be omitted. In this case, it is possible to reduce the number of measurement points and shorten the measurement time.

Figure 15:
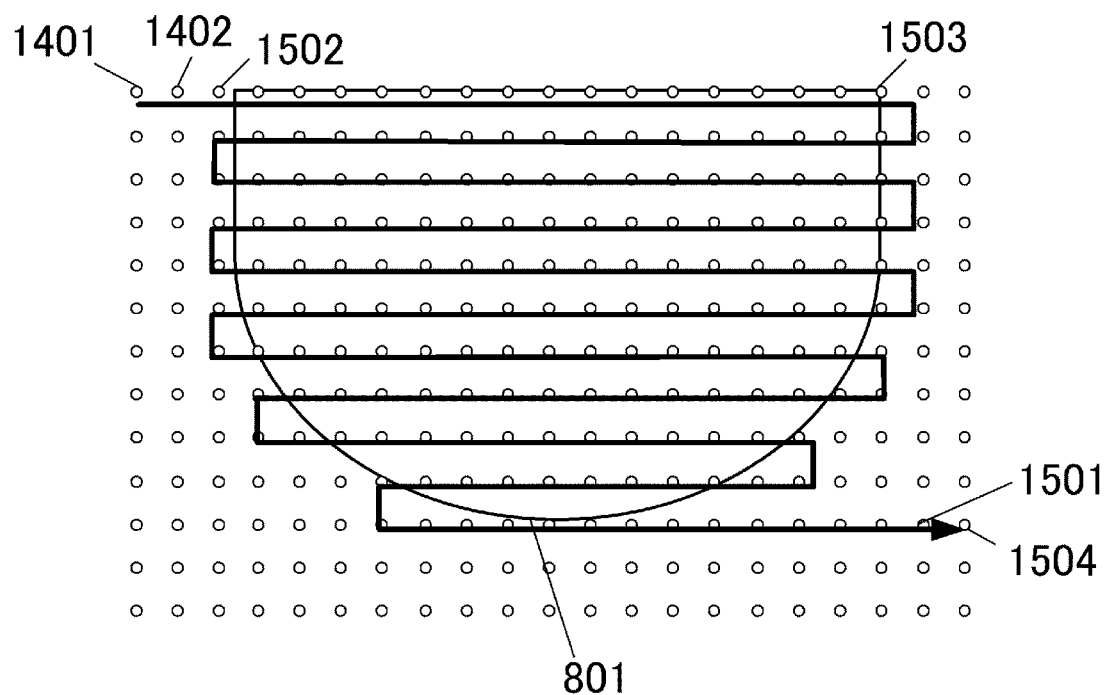
FIG. 15 is a diagram illustrating measurement points and a moving direction in a modification of the second embodiment of the invention.

This modification will be described with reference to FIG. 15. In general, the probe 802 is moved in the horizontal direction to perform measurement. When the left and right boundary points (for example, measurement points 1502 and 1503) of the object is detected from a change in the result of the position determining process, the movement of the object to the measurement points outside the boundary is omitted and the probe is moved in the vertical direction. When the scanning range is changed in this way, it is possible to prevent measurement in the region where there is no object. In addition, when the point which is suitable to acquire the photoacoustic signal is not detected even though the probe is moved to an end measurement point 1504, the measurement process ends without moving the probe any further in the vertical direction. The probe scans the object along an arrow 1501 illustrated in FIG. 15. In this way, it is possible to reduce the measurement time.

Third Embodiment

Next, a third embodiment of the invention will be described. The third embodiment differs from the first and second embodiments in that, when the position of the object is determined, the received ultrasound echo signals are not read to be analyzed, but the position of the object is determined on the basis of the ultrasound echo signals obtained by newly transmitting and receiving ultrasound waves in the vicinity of the target point. That is, before light is radiated in order to receive the photoacoustic wave, an ultrasound wave beam for determination is transmitted and received.

Figure 11:
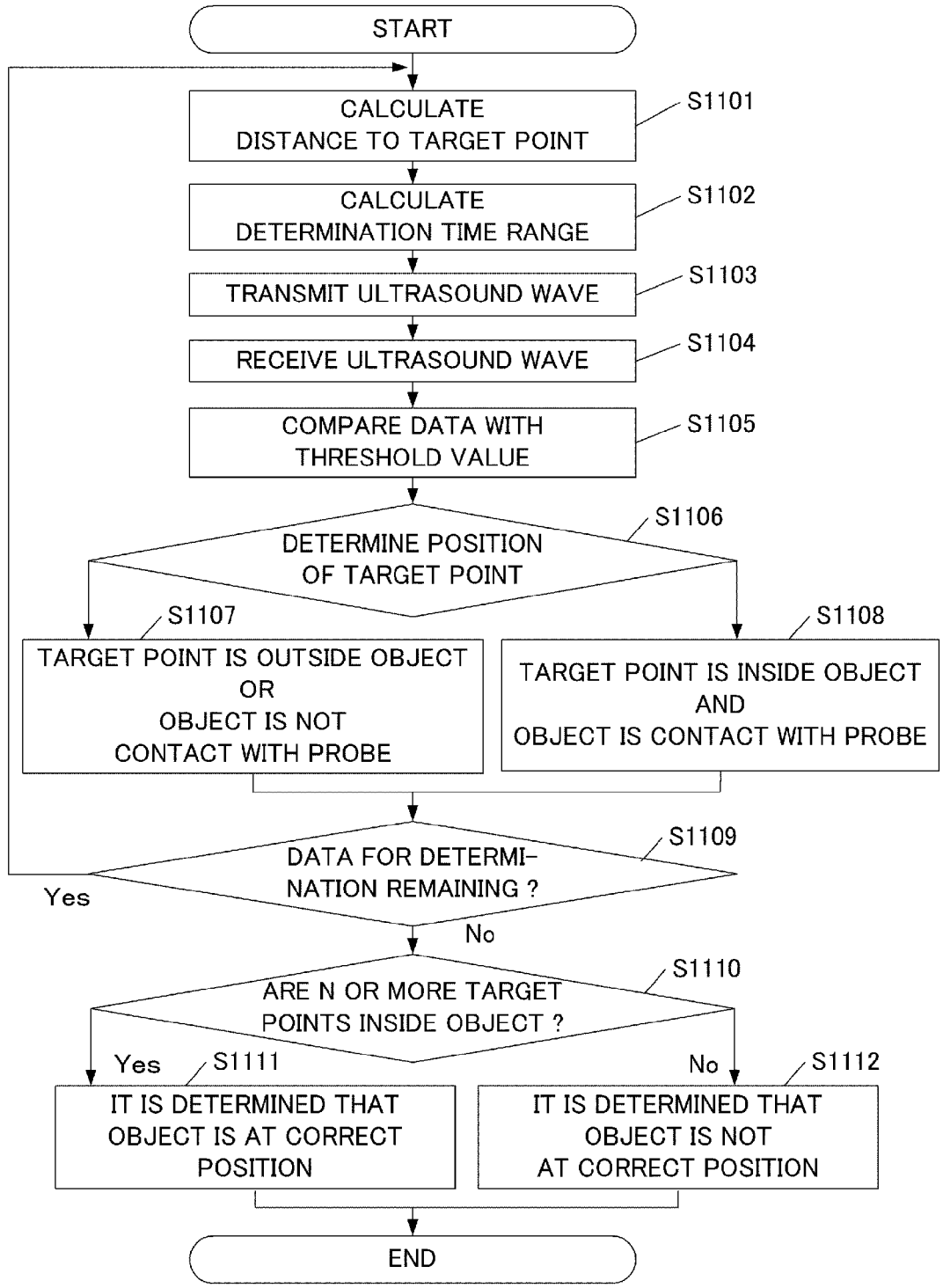
FIG. 11 is a flowchart illustrating a position determining process according to a third embodiment of the invention.

The block diagram and the operation flow according to the third embodiment of the invention are the same as those according to the first and second embodiments and thus the description thereof will not be repeated. FIG. 11 illustrates the flow of an object position determining process according to this embodiment. In Steps S1101 and S1102, a CPU 201 calculates the distance to the target point and the determination time range, similarly to the above-described embodiments.

Then, in Step S1103, the CPU 201 instructs a transmitting circuit 202 to transmit an ultrasound wave beam 901 for determination to a target point 903. In this case, since it is sufficient for the ultrasound wave beam for determination to have intensity to reach the target point 903, it is possible to reduce the voltage of the transmitting circuit and reduce the time required to transmit and receive the ultrasound wave beam for determination. Then, in Step S1104, a receiving circuit 203 receives the ultrasound echo signal of the ultrasound wave beam 901 for determination and digitalizes the received ultrasound echo signal.

Then, in Step S1105, in the ultrasound echo signal data obtained from the received ultrasound wave beam 901 for determination, data in the determination time range calculated in Step S1102 is compared with a predetermined threshold value, similarly to the first and second embodiments. In this case, the receiving circuit 203 may compare the echo signal data of the ultrasound wave beam 901 for determination with the threshold value, thereby increasing the speed of the determining process. Then, from Steps S1106 to S1112, the same processes as those from Step S505 to Step S511 in the above-described embodiments are performed to determine whether the object 801 is set at a correct position.

In this embodiment, the ultrasound wave beam acquired immediately before pulsed light is radiated is used to perform determination. In this way, it is possible to accurately determine the positional relation between the object and the probe even when the relative position between the probe and the object is changed while taking time from the transmission and reception of the ultrasound wave in Steps S401 to S403 to the acquisition of the photoacoustic signal in Step S404.

Fourth Embodiment

Next, a fourth embodiment of the invention will be described. The fourth embodiment of the invention differs from the second embodiment in that the light emission hole is away from the probe.

Figure 12:
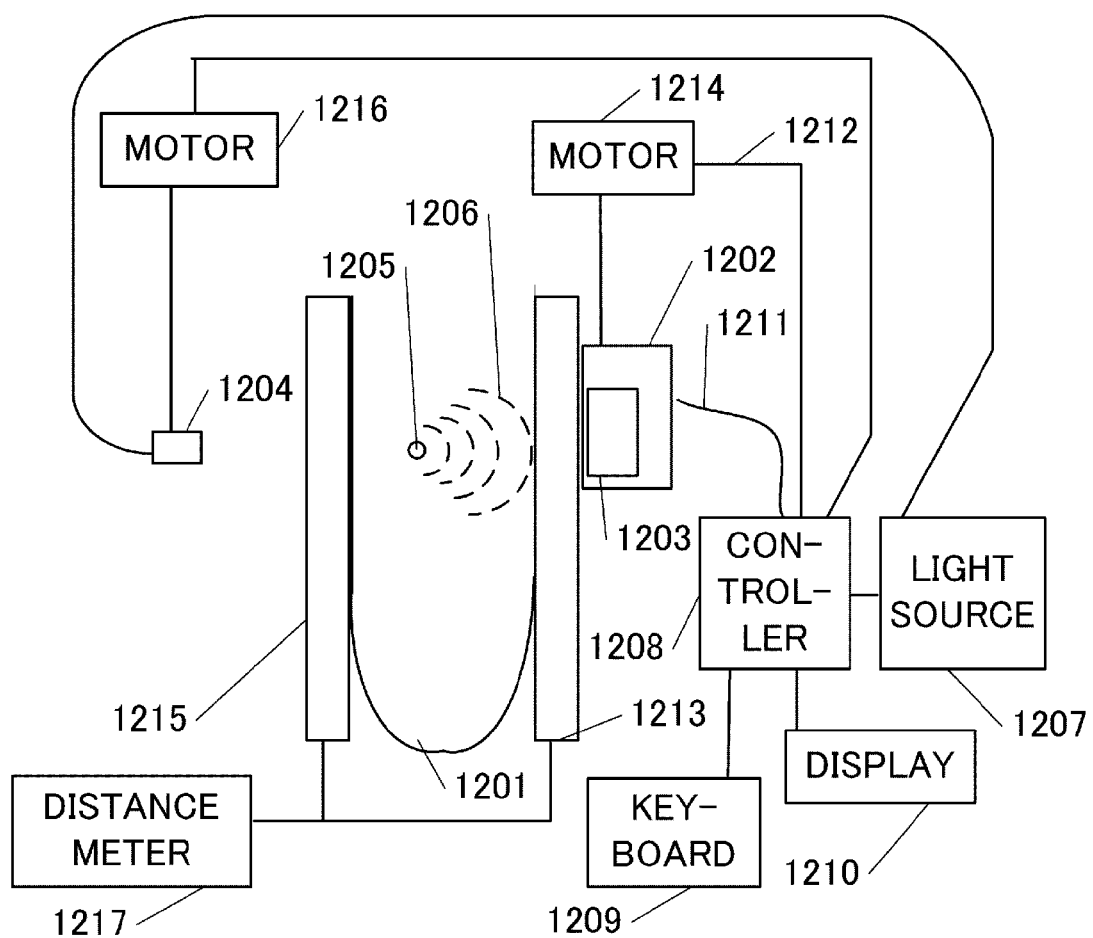
FIG. 12 is a block diagram illustrating a structure according to a fourth embodiment of the invention.

FIG. 12 is a block diagram illustrating the structure of a photoacoustic apparatus according to the second embodiment of the invention. In FIG. 12, an object 1201, a transducer 1203, a light absorption part 1205, a photoacoustic wave 1206, a light source 1207, and a controller 1208 are the same as those in the second embodiment and thus the description thereof will not be repeated. In FIG. 12, a keyboard 1209, a display 1210, a cable 1211, an optical fiber 1212, a compression plate 1213, and a motor 1214 are the same as those in the second embodiment and thus the description thereof will not be repeated.

Reference numeral 1202 refers to a probe which can transmit and receive ultrasound waves. Reference numeral 1204 refers to a light emission hole. Unlike the second embodiment, the light emission hole 1204 is disposed opposite to the probe 1202 with the object interposed therebetween. Reference numeral 1215 refers to a compression plate which is opposite to the compression plate 1213 with the object 1201 interposed therebetween. The compression plate 1213 and the compression plate 1215 fix the object 1201 therebetween. Reference numeral 1216 refers to a mechanism which moves the light emission hole 1204 for two-dimensional scanning. The mechanism 1216 includes, for example, a motor, an X-Y stage, and an encoder.

Reference numeral 1217 refers to a sensor which measures the distance between the compression plate 1213 and the compression plate 1215. The sensor 1217 is a potentiometer. In the photoacoustic apparatus according to this embodiment, the user fixes the object 1201 between the compression plates in advance and operates the keyboard 1209 to input a measurement start instruction. The controller 1208 receives the measurement start instruction and two-dimensionally moves the probe 1202 using the motor 1214 while having the probe 1202 contacting with the compression plate 1213. The motor 1216 close to the light emission hole moves the light emission hole 1204 in synchronization with the probe 1202. In this way, the light emission hole 1204 is constantly disposed in front of the probe 1202. An ultrasound echo signal and a photoacoustic signal are acquired according to the flow illustrated in FIG. 10 while the probe 1202 and the light emission hole 1204 are moved.

FIG. 13 is an enlarged view illustrating the periphery of the object 1201 and the probe 1202 in the fourth embodiment of the invention. Reference numeral 1301 refers to an ultrasound wave beam for determination. Reference numeral 1302 refers to a target point on the ultrasound wave beam 1301 for determination. In this embodiment, the target point 1302 is an intersection point between the compression plate 1215 and an optical path 1303. Further, a determination start point 1304 is an intersection point between the compression plate 1213 and the optical path 1303. Reference numeral 1303 refers to an optical path of light from the light emission hole 1204 to the object 1201. Reference numeral 1305 refers to an intersection point between a surface of the object 1201 close to the compression plate 1215 and the ultrasound wave beam 1301.

Figure 13A:
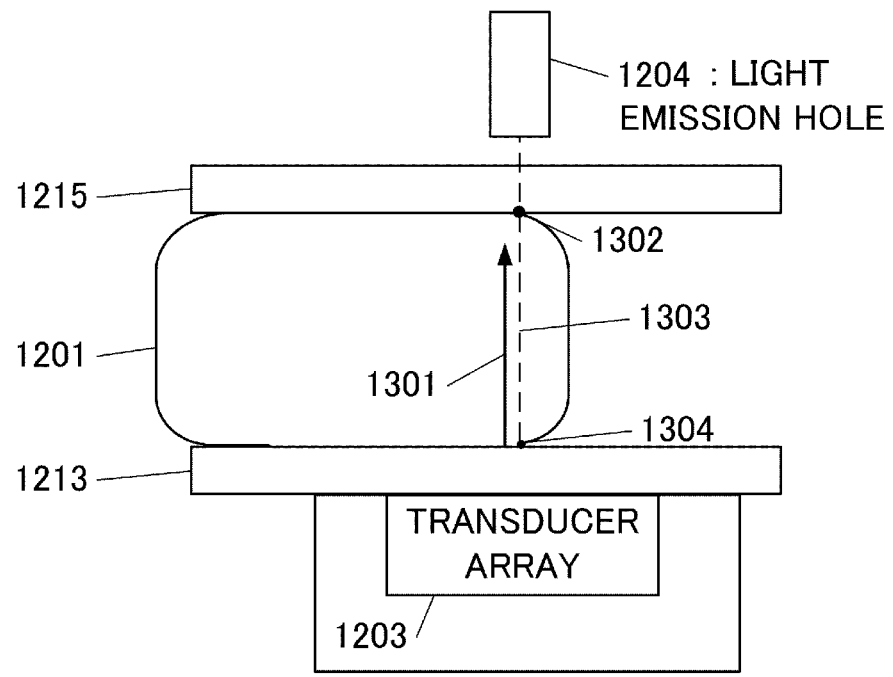
FIGS. 13A and 13B are diagrams illustrating the positional relation in the vicinity of an object in the fourth embodiment of the invention.
Figure 13B:
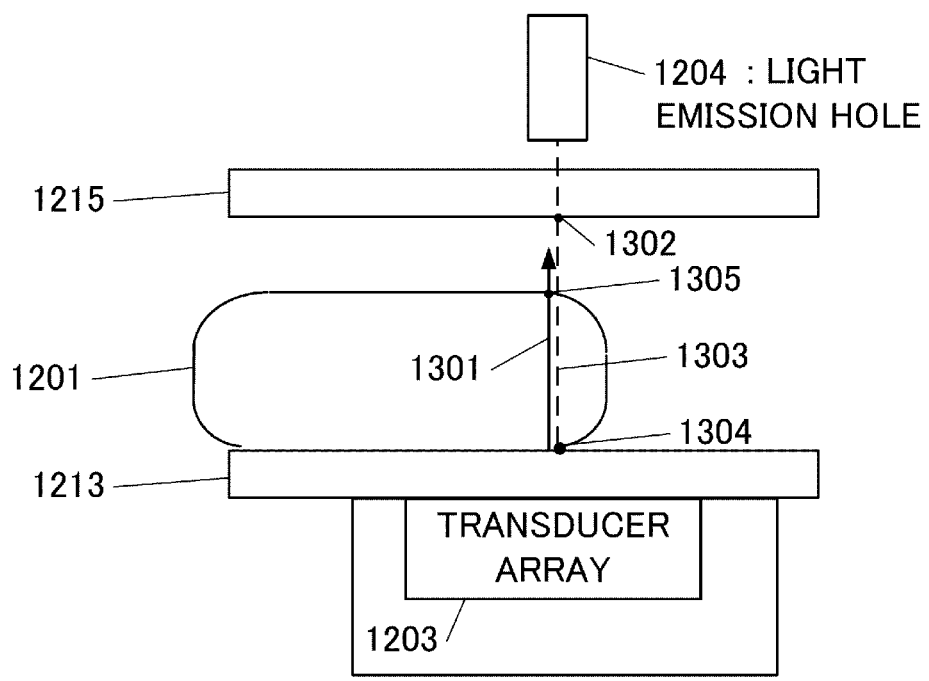

FIG. 13A illustrates an example in which the object 1201 is fixed between the compression plate 1213 and the compression plate 1215 and is then correctly compressed. FIG. 13B illustrates an example in which the object is interposed between the compression plate 1213 and the compression plate 1215 with a gap between the object and compression plate 1215 and is not correctly fixed therebetween. In addition, in some cases, when a part other than the object, for example, a hand other than a breast, is placed on the compression plate, the positional relation illustrated in FIG. 13B is established. In addition, in some cases, a gap may be partially formed between the object and the compression plate.

In this embodiment, the flow of the determining process is the same as that in the flowchart illustrated in FIG. 5. However, in this embodiment, the distance between the compression plate 1213 and the compression plate 1215 varies depending on the kind of object 1201. Therefore, the position of the target point 1302 also varies according to a measurement. Distance meter 1217 is used to measure the variation and the measured variation is reflected to calculate the distance to the target point. That is, in Step S501 of FIG. 5, the value which is stored in the memory 206 in advance is not used as the distance to the target point, but the distance between the compression plates 1213 and 1215 measured by the distance meter 1217 is used. The subsequent steps will be taken the same as those in the second embodiment. In this embodiment, the period from the time when the ultrasound echo from the determination start point 1304 reaches the target point 1302 to the time when the ultrasound echo from the target point 1302 returns to the probe 1202 is the determination time range.

In the positional relation illustrated in FIG. 13A, there is no air between the ultrasound wave beam 1301 for determination and the target point 1302 and the probe 1202, the compression plate 1213, and the object 1201 come into tight contact with each other. Therefore, most of the transmitted ultrasound wave beams can be propagated through the object and then reach the target point 1302. The voltage of the ultrasound echo signal between the determination start point 1304 and the target point 1302 is greater than the threshold value v2 and smaller than the threshold value v1. As a result, in Step S507, it is determined that the target point is inside the object and the contact between the object and the probe is sufficient. Finally, in Step S510, it is determined that the object is set at a correct position and it is possible to acquire the photoacoustic signal.

In the positional relation illustrated in FIG. 13B, since there is air between the object 1201 and the compression plate 1215, most of the ultrasound wave beams 1301 for determination are reflected on a boundary point 1305 between the surface of the object 1201 and air. Therefore, in the ultrasound echo signal, a high-voltage signal appears in the determination time range and then the signal level is reduced. As a result, in Step S506, it is determined that the target point 1302 is outside the object. Finally, in Step S511, it is determined that the object is not set at a correct position and it is difficult to acquire the photoacoustic signal.

In this embodiment, light is emitted in a direction opposite to the probe 1202. However, in the photoacoustic apparatus according to the invention, the emission direction of light is not limited thereto. Even when light is emitted from different directions, the target point may be set at an intersection point between the optical path and the ultrasound wave beam for determination. In this way, it is possible to determine the position of the object. Even when the light emission hole 1204 is away from the probe 1202, the above-mentioned method makes it possible to determine whether the object is set at a correct position so the photoacoustic signal can be acquired. In addition, even when the position of the target point is changed depending on the object, it is possible to accurately determine the position of the object.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-102842, filed on May 2, 2011, which is hereby incorporated by reference herein in its entirety.

The invention claimed is:

1. An object information acquiring apparatus comprising:
a light irradiating unit that irradiates an object with light to generate a photoacoustic wave;
a probe having a transducer that receives the photoacoustic wave and outputs a photoacoustic signal based on the received photoacoustic wave, and wherein said transducer transmits and receives an ultrasound wave beam to and from the object, and outputs an ultrasound echo signal based on the received ultrasound wave beam;
a determining unit that determines whether the object is disposed on a direction of light irradiation from said light irradiating unit based on the ultrasound echo signal output from said transducer; and
a controller that controls said light irradiating unit,
wherein said transducer transmits the ultrasound wave beam to a target point on the direction of light irradiation from said light irradiating unit, and
wherein when said determining unit determines that there is no object on the direction of light irradiation from said light irradiating unit, said controller controls said light irradiating unit not to radiate light.

2. The object information acquiring apparatus according to claim 1, wherein, when the voltage of the ultrasound echo signal exceeds a predetermined threshold value v1, said determining unit determines that the object is not disposed on the direction of light irradiation from said light irradiating unit.

3. The object information acquiring apparatus according to claim 2, wherein said determining unit sets, as a determination time range, a period from the time when said transducer transmits the ultrasound wave beam to the target point on the direction of light irradiation from said light irradiating unit to the time which is calculated based on the distance between said transducer and the target point and performs the determination on the ultrasound echo signal acquired in the determination time range.

4. The object information acquiring apparatus according to claim 3, wherein the determination time range is from the time when said transducer transmits the ultrasound wave beam to the time calculated by dividing a value that is twice the distance between said transducer and the target point by an internal sound speed of the object.

5. The object information acquiring apparatus according to claim 3, wherein, when there is a voltage of an ultrasound echo signal which exceeds the predetermined threshold value v1 in the determination time range, said determining unit determines that the object is not disposed on the direction of light irradiation from said light irradiating unit.

6. The object information acquiring apparatus according to claim 5, wherein the predetermined threshold value v1 exceeds the voltage of the ultrasound echo signal acquired when the ultrasound wave beam is reflected from the inside of the object, said determining unit determines that the object is disposed on the direction of light irradiation from said light irradiating unit.

7. The object information acquiring apparatus according to claim 3, wherein, only when the voltage of the ultrasound echo signal exceeds the predetermined threshold value v1, and then falls down to a threshold value v2 which is less than the predetermined threshold value v1, said determining unit determines that the object is not disposed on the direction of light irradiation from said light irradiating unit.

8. The object information acquiring apparatus according to claim 7, further comprising a receiving circuit that processes the signal acquired by said transducer, wherein the noise level of said receiving circuit determines the threshold value v2.

9. The object information acquiring apparatus according to claim 3, further comprising:
a holding member that holds the object, wherein said transducer transmits and receives the ultrasound wave beam to and from the object through said holding member, and wherein said determining unit excludes the range in which the ultrasound wave beam transmitted from said transducer passes through said holding member from the determination time range and performs the determination.

10. The object information acquiring apparatus according to claim 3, further comprising:
a holding member that holds the object; and
a scanning unit that moves said probe and said light irradiating unit provided on said holding member in synchronization with each other,
wherein said determining unit performs the determination at each position to which said transducer is moved by said scanning unit, and
wherein, when it is determined that the object is not disposed on the direction of light irradiation from said light irradiating unit, said scanning unit changes the movement range of said transducer and said light irradiating unit.

11. The object information acquiring apparatus according to claim 3, further comprising:
two holding members that hold the object therebetween; and
a distance meter that measures the distance between said two holding members,
wherein said probe and said light irradiating unit are provided on said holding members so as to be opposite to each other with the object interposed therebetween, and
wherein said determining unit changes the position of the target point according to the distance between said two holding members.

12. The object information acquiring apparatus according to claim 1,
wherein said determining unit determines whether multiple reflection occurs in the surface of said transducer based on the ultrasound echo signal, and
when it is determined that multiple reflection occurs, said determining unit determines that the object is absent.

13. The object information acquiring apparatus according to claim 12, wherein said determining unit determines that multiple reflection occurs when a peak of a predetermined frequency component appears in the ultrasound echo signal corresponding to the surface of said transducer.

14. The object information acquiring apparatus according to claim 1, further comprising an image processor that generates internal image data of the object using at least the photoacoustic signal,
wherein said image processor generates the internal image data of the object using the ultrasound echo signal, and
wherein said determining unit performs the determination using the ultrasound echo signal which is acquired in order to generate image data.

15. The object information acquiring apparatus according to claim 1, further comprising a controller that controls the transmitting and receiving operation of said transducer,
wherein said transducer transmits and receives an ultrasound wave beam for determination which is used by said determining unit before said light irradiating unit radiates light, and
wherein said determining unit performs the determination using the ultrasound echo signal acquired by the transmission and reception of the ultrasound wave beam for determination.

16. The object information acquiring apparatus according to claim 1, wherein the light irradiating unit irradiates the object with light from a position different from another position at which the transducer transmits and receives the ultrasound wave beam.

17. The object information acquiring apparatus according to claim 1, wherein a position at which the light irradiating unit irradiates the object with light and another position at which the transducer transmits and receives the ultrasound wave beam are at the same side of the object.

18. The object information acquiring apparatus according to claim 1, wherein a position at which the light irradiating unit irradiates the object with light and another position at which the transducer transmits and receives the ultrasound wave beam are at different sides of the object.

19. The object information acquiring apparatus according to claim 1, wherein
a plurality of the transducers are disposed in array, and
the controller controls to perform electronic scanning with a plurality of the ultrasound wave beams.

20. A method of controlling an object information acquiring apparatus, comprising:
transmitting and receiving, by a transducer, an ultrasound wave beam to and from an object and outputting an ultrasound echo signal;
determining, by a determining unit, whether the object is disposed on an direction of light irradiation from a light irradiating unit based on the ultrasound echo signal output from the transducer;
irradiating, by the light irradiating unit, the object with light such that a photoacoustic wave is generated; and
receiving, by the transducer, the photoacoustic wave and outputting a photoacoustic signal; and
controlling, by a controller, said light irradiating unit,
wherein, in the transmitting and receiving step, the transducer transmits the ultrasound wave beam to a target point on the direction of light irradiation from the light irradiating unit, and
wherein, when said determining unit determines that there is no object on the direction of light irradiation from said light irradiating unit, said controller controls said light irradiating unit not to radiate light.

21. An object information acquiring apparatus comprising:
a light irradiating unit that irradiates an object with light to generate a photoacoustic wave;
a probe having a transducer that receives the photoacoustic wave and outputs a photoacoustic signal based on the received photoacoustic wave, and said transducer transmits and receives an ultrasound wave beam to and from the object, and outputs an ultrasound echo signal based on the received ultrasound wave beam;
a determining unit that determines whether the light from said light irradiating unit is incident on the object based on the ultrasound echo signal output from said transducer; and
a controller that controls said light irradiating unit,
wherein said transducer transmits the ultrasound wave beam to a target point on a direction of light irradiation from said light irradiating unit, and
wherein, when said determining unit determines that the light from said light irradiating unit is not incident on the object, said controller controls said light irradiating unit not to radiate light.

* * * * *